United States Patent
Wallace et al.

(10) Patent No.: US 8,512,729 B2
(45) Date of Patent: *Aug. 20, 2013

(54) FRAGMENTED POLYMERIC COMPOSITIONS AND METHODS FOR THEIR USE

(71) Applicants: Baxter International Inc., Deerfield, IL (US); Baxter Healthcare S.A., Glattpark (Opfikon) (CH)

(72) Inventors: Donald G. Wallace, Menlo Park, CA (US); Cary J. Reich, Los Gatos, CA (US); Narinder S. Shargill, Dublin, CA (US); Felix Vega, San Francisco, CA (US); A. Edward Osawa, San Francisco, CA (US); Zhen Qian-Wallis, Fremont, CA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/665,475

(22) Filed: Oct. 31, 2012

(65) Prior Publication Data
US 2013/0108611 A1    May 2, 2013

Related U.S. Application Data

(63) Continuation of application No. 13/174,963, filed on Jul. 1, 2011, now Pat. No. 8,303,981, which is a continuation-in-part of application No. 09/553,969, filed on Apr. 21, 2000, now abandoned, which is a continuation-in-part of application No. 09/032,370, filed on Feb. 27, 1998, now Pat. No. 6,066,325, which is a continuation-in-part of application No. 08/903,674, filed on Jul. 31, 1997, now Pat. No. 6,063,061, which is a continuation-in-part of application No. 08/704,852, filed on Aug. 27, 1996, now abandoned, which is a continuation-in-part of application No. 12/176,945, filed on Jul. 21, 2008, now Pat. No. 8,383,141, which is a continuation of application No. 09/908,464, filed on Jul. 17, 2001, now Pat. No. 7,435,425.

(60) Provisional application No. 60/050,437, filed on Jun. 18, 1997.

(51) Int. Cl.
*A61F 13/00* (2006.01)
*A61F 2/00* (2006.01)
*A61K 9/44* (2006.01)

(52) U.S. Cl.
USPC ............ 424/422; 424/443; 424/445; 424/489

(58) Field of Classification Search
None
See application file for complete search history.

(56) References Cited

U.S. PATENT DOCUMENTS 2,507,244 A   5/1950   Correll
2,558,395 A   6/1951   Studer (Continued)

FOREIGN PATENT DOCUMENTS

CN    1270240 A    10/2000
EP    0282316 A2    9/1988

(Continued)

OTHER PUBLICATIONS

Ansell, J., et al., "Gelfoam and Autologous Clot Embolization: Effect on Coagulation," *Investigative Radiology*, 1978, vol. 13, pp. 115-120.

(Continued)

*Primary Examiner* — Lakshmi Channavajjala
(74) *Attorney, Agent, or Firm* — Kikpatrick Townsend & Stockton LLP

(57) ABSTRACT

Cross-linked hydrogels comprise a variety of biologic and non-biologic polymers, such as proteins, polysaccharides, and synthetic polymers. Such hydrogels preferably have no free aqueous phase and may be applied to target sites in a patient's body by extruding the hydrogel through an orifice at the target site. Alternatively, the hydrogels may be mechanically disrupted and used in implantable articles, such as breast implants. When used in vivo, the compositions are useful for controlled release drug delivery, for inhibiting post-surgical spinal and other tissue adhesions, for filling tissue divots, tissue tracts, body cavities, surgical defects, and the like.

18 Claims, 6 Drawing Sheets

(56) References Cited

U.S. PATENT DOCUMENTS

| | | |
|---|---|---|
| 3,089,815 A | 5/1963 | Kupelwieser et al. |
| 4,006,220 A | 2/1977 | Gottlieb |
| 4,013,078 A | 3/1977 | Field |
| 4,124,705 A | 11/1978 | Rothman et al. |
| 4,164,559 A | 8/1979 | Miyata et al. |
| 4,179,400 A | 12/1979 | Tsao et al. |
| 4,265,233 A | 5/1981 | Sugitachi et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,424,208 A | 1/1984 | Wallace et al. |
| 4,453,939 A | 6/1984 | Zimmerman et al. |
| 4,482,386 A | 11/1984 | Wittwer et al. |
| 4,515,637 A | 5/1985 | Cioca |
| 4,536,387 A | 8/1985 | Sakamoto et al. |
| 4,540,410 A | 9/1985 | Wood et al. |
| 4,543,332 A | 9/1985 | Jao et al. |
| 4,554,156 A | 11/1985 | Fischer |
| 4,600,574 A | 7/1986 | Lindner et al. |
| 4,640,834 A | 2/1987 | Eibl et al. |
| 4,655,211 A | 4/1987 | Sakamoto et al. |
| 4,746,514 A | 5/1988 | Warne |
| 4,749,689 A | 6/1988 | Miyata et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,885,161 A | 12/1989 | Cornell |
| 4,891,359 A | 1/1990 | Saferstein et al. |
| 4,925,677 A | 5/1990 | Feijen |
| 4,946,870 A | 8/1990 | Partain, III et al. |
| 5,007,916 A | 4/1991 | Linsky et al. |
| 5,017,229 A | 5/1991 | Burns et al. |
| 5,023,082 A | 6/1991 | Friedman et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,658,592 A | 8/1997 | Tanihara et al. |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,752,974 A | 5/1998 | Rhee et al. |
| 5,770,229 A | 6/1998 | Tanihara et al. |
| 5,853,749 A | 12/1998 | Hobbs |
| 5,856,356 A | 1/1999 | Tsouderos et al. |
| 5,861,043 A | 1/1999 | Carn |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,997,895 A | 12/1999 | Narotam et al. |
| 6,063,061 A | 5/2000 | Wallace et al. |
| 6,066,325 A | 5/2000 | Wallace et al. |
| 6,110,484 A | 8/2000 | Sierra |
| 6,129,761 A | 10/2000 | Hubbell |
| 6,132,759 A * | 10/2000 | Schacht et al. ............ 424/445 |
| 6,166,130 A | 12/2000 | Rhee et al. |
| 6,179,872 B1 | 1/2001 | Bell et al. |
| 6,277,394 B1 | 8/2001 | Sierra |
| 6,312,474 B1 | 11/2001 | Francis et al. |
| 6,312,725 B1 | 11/2001 | Wallace et al. |
| 6,328,229 B1 | 12/2001 | Duronio et al. |
| 6,458,386 B1 | 10/2002 | Schacht et al. |
| 6,458,889 B1 | 10/2002 | Trollsas |
| 6,624,245 B2 | 9/2003 | Wallace et al. |
| 6,706,690 B2 | 3/2004 | Reich et al. |
| 6,831,058 B1 * | 12/2004 | Ikada et al. ............ 514/9.1 |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 8,303,981 B2 * | 11/2012 | Wallace et al. ............ 424/443 |
| 8,357,378 B2 * | 1/2013 | Wallace et al. ............ 424/400 |
| 2002/0193448 A1 | 12/2002 | Wallace et al. |
| 2003/0064109 A1 | 4/2003 | Qian et al. |
| 2006/0147492 A1 | 7/2006 | Hunter et al. |
| 2006/0167561 A1 | 7/2006 | Odar et al. |
| 2008/0085316 A1 | 4/2008 | Qian et al. |
| 2008/0091277 A1 | 4/2008 | Deusch et al. |
| 2008/0286376 A1 | 11/2008 | Qian et al. |
| 2009/0142396 A1 | 6/2009 | Odar et al. |
| 2010/0028309 A1 | 2/2010 | Odar et al. |
| 2010/0292717 A1 | 11/2010 | Petter-Puchner et al. |
| 2010/0318048 A1 | 12/2010 | Hoeffinghoff et al. |

FOREIGN PATENT DOCUMENTS

| | | |
|---|---|---|
| EP | 0376931 | 7/1990 |
| EP | 0132983 B2 | 12/1991 |
| EP | 0493387 | 7/1992 |
| EP | 0891193 | 1/1999 |
| EP | 0612252 B1 | 5/1999 |
| EP | 1084720 A1 | 3/2001 |
| EP | 1283063 A1 | 2/2003 |
| EP | 1484070 A1 | 12/2004 |
| EP | 1414370 B1 | 4/2007 |
| JP | 51-125156 | 11/1976 |
| JP | 59-113889 | 6/1984 |

| | | |
|---|---|---|
| JP | 05308969 | 11/1993 |
| JP | 6-254148 | 9/1994 |
| JP | 08-024325 | 1/1996 |
| JP | 9-504719 | 5/1997 |
| JP | 07090241 | 4/2007 |
| KR | 10-1991-0007847 B1 | 10/1991 |
| WO | 86/00912 | 2/1986 |
| WO | 92/21354 | 12/1992 |
| WO | 92/22252 | 12/1992 |
| WO | 94/27630 A1 | 12/1994 |
| WO | 95/12371 | 5/1995 |
| WO | 95/15747 | 6/1995 |
| WO | 96/04025 | 2/1996 |
| WO | 96/06883 | 3/1996 |
| WO | 96/10374 | 4/1996 |
| WO | 96/10428 | 4/1996 |
| WO | 96/14368 | 5/1996 |
| WO | 96/39159 | 12/1996 |
| WO | 97/37694 A1 | 10/1997 |
| WO | 98/08550 A1 | 3/1998 |
| WO | 99/13902 | 3/1999 |
| WO | 02/22184 | 3/2002 |
| WO | 02/070594 | 9/2002 |
| WO | 03/007845 | 1/2003 |
| WO | 2004/108179 | 12/2004 |
| WO | 2006/031358 | 3/2006 |
| WO | 2006/118460 | 11/2006 |
| WO | 2007/001926 | 1/2007 |
| WO | 2007/137839 | 12/2007 |
| WO | 2008/016983 | 2/2008 |

OTHER PUBLICATIONS

Barrow, D.L., et al., "The Use of Greater Omentum Vascularized Free Flaps for Neurosurgical Disorders Requiring Reconstruction," *Journal of Neurosurgery*, 1984, vol. 60, pp. 305-311.

Barton, B., et al., "Fibrin Glue as a Biologic Vascular Patch—A Comparative Study," *Journal of Surgical Research*, 1986, vol. 40, 1 page; abstract retrieved from http://www.ncbi.nlm.nih.gov on Jan. 3, 2001.

Baxter, "TissuFleece E, TissuCone E and TissuFoil E: Biomaterials by Baxter: Basic scientific information," 2003, 9 pages.

Baxter, "Product Catalogue: Collagen," 2006, 4 pages, retrieved from http://www.baxter-ecommerce.com/ecatalog on Feb. 2, 2006.

Boyers, S., et al., "Reduction of Postoperative Pelvic Adhesions in the Rabbit with Gore-Tex Surguical Membrane," *Fertility and Sterility*, 1988, vol. 49, No. 6, pp. 1066-1070.

Author Unknown, "Controlled Drug Delivery: vol. 1: Basic Concepts," Ed. Stephen D. Bruck, Boca Raton, FL, USA, CRC Press, Inc., 1983, 4 pages.

Cantor, M., et al., "Gelfoam and Thrombin in Gastroduodenal Bleeding: An Experimental Study", *Journal of Laboratory and Clinical Medicine*, 1950, vol. 35, No. 6, pp. 890-893.

Cantor, M., et al., "Gelfoam and Thrombin in Treatment of Massive Gastroduodenal Hemmorhage: A Preliminary Report," *The American Journal of Surgery*, 1950, vol. 80, Issue 7, pp. 883-887.

Cantor, M., et al., "Gelfoam and Thrombin in Treatment of Massive Upper Gastrointestinal Hemorrhage," *American Journal of Surgery*, 1951, vol. 82, No. 2, pp. 230-235.

Chaplin, J.M., et al., "Use of an Acellular Dermal Allograft for Dural Replacement: An Experimental Study," *Neurosurgery*, 1999, vol. 45, No. 2, pp. 320-327.

Cheung, D., et al., "Mechanism of Crosslinking of Proteins by Glutaraldehyde IV: In Vitro and In Vivo Stability of a Crosslinked Collagen Matrix," *Connective Tissue Research*, 1990, vol. 25, pp. 27-34.

Chuang, V., et al., "Sheath Needle for Liver Biopsy in High-Risk Patients," *Radiology*, 1988, vol. 166, pp. 261-262.

Collins, D., et al., "Enemata of Gelfoam-Milk Suspension Combined with Thrombin-Solution to Control Massive Hemorrhage Following Anorectal Surgery," *The American Journal of Proctology*, 1951, vol. 2, pp. 60-63.

Collins, R., et al., "Use of Collagen Film as a Dural Substitute: Preliminary Animal Studies," *Journal of Biomedical Materials Research*, 1991, vol. 25, pp. 267-276.

Edgerton, M., et al., "Vascular Hamartomas and Hemangiomos: Classification and Treatment," *Southern Medical Journal*, 1982, vol. 75, No. 12, pp. 1541-1547.

Filippi, R., et al., "Bovine Pericardium for Duraplasty: Clinical Results in 32 Patients," *Neurosurgical Review*, 2001, vol. 20, pp. 103-107.

Baxter, "GentaFleece Collagen Fleece—Version 5: Instructions for Use—Collagen sponge with antibiotic protection for surgical use," Retrieved from http://www.advancingbiosurgery.com/en_EU/downloads/ifu_gentafleece.pdf on Mar. 2002, 2 pages. English portion second column of first page.

Gibble, et al., "Fibrin glue: the perfect operative sealant?," *Reviews: Transfusion*, 1990, vol. 30, No. 8, pp. 741-747.

Heller, J., et al., "Release of Norethindrone from Poly(Ortho Esters)," *Polymer Engineering and Science*, 1981, vol. 21, pp. 727-731.

Hieb, L., et al., "Spontaneous Postoperative Cerebrospinal Fluid Leaks Following Application of Anti-Adhesion Barrier Gel," *SPINE*, vol. 26, No. 7, pp. 748-751, 2001.

Hood, D., et al., "Efficacy of Topical Hemostat Floseal Matrix in Vascular Surgery," 24th World Congress of the International Society for Cardiovascular Surgery, Sep. 12-16, 1999, 2 pages.

Hotz, G., et al., "Collagen and Fibrin as Biologic Binders from Granular Hydroxyapatite," *Deutsche Zeitschrift fur Mund-, Kiefer- und Gesichts-Chirurgie*, 1989, vol. 13, No. 4, pp. 296-300. Abstract retrieved from http://www.ncbi.nlm.nih.gov/ on Jan. 3, 2001.

Jeong, B., et al., "Biodegradable Block Copolymers as Injectable Drug-Delivery Systems," *Nature*, 1997, vol. 388, pp. 860-862.

Jonas, R., et al., "A new sealant for knitted Dacron prostheses: Minimally cross-linked gelatin," *Journal of Vascular Surgery*, 1988, vol. 7, No. 3, pp. 414-419.

Kim, K., et al., "Reduction in Leg Pain and Lower-Extremity Weakness with Oxiplex/SP Gel for 1 Year after Laminectomy, Laminotomy, and Disectomy," *Neurosurgical Focus*, 2004, vol. 17, pp. 1-6.

Kline, D., et al., "Dural Replacement with Resorbable Collagen," *Archives of Surgery*, 1965, vol. 91, pp. 924-929.

Knopp, U., "A New Collagen Foil Versus a Cadaveric Dura Graft for Dural Defects—A Comparative Animal Experimental Study", *European Association of Neurosurgical Societies—Proceedings of the 12th European Congress of Neurosurgery*, Lisbon, 2003, 17 pages.

Krill, D., et al., "Topical Thrombin and Powdered Gelfoam: An Efficient Hemostatic Treatment for Surgery," *Journal of Tennessee Dental Association*, 1986, vol. 66, No. 2, pp. 26-27.

Kuhn, J., et al., "Bilateral Subdural Haematomata and Lumbar Pseudomeningocele Due to a Chronic Leakage of Liquor Cerebrospinalis after a Lumbar Disectomy with the Application of ADCON-L Gel," *Journal of Neurology, Neurosurgery & Psychiatry*, 2005, vol. 76, pp. 1031-1033.

Langer, R., et al., "Chemical and Physical Structure of Polymers as Carriers for Controlled Release of Bioactive Agents: A Review," *Journal of Macromolecular Science—Reviews in Macromolecular Chemistry and Physics*, 1983, C23, pp. 61-126.

Laquerriere, A., et al., "Experimental Evaluation of Bilayered Human Collagen as a Dural Substitute," *Journal of Neurosurgery*, 1993, vol. 78, pp. 487-491.

Larson, P., "Topical Hemostatic Agents for Dermatologic Surgery," *Journal of Dermatologic Surgery & Oncology*, 1988, vol. 14, pp. 623-632.

Le, A., et al., "Unrecognized Durotomy After Lumbar Discectomy: A Report of Four Cases Associated with the Use of ADCON-L," *SPINE*, 2001, vol. 26, No. 1, pp. 115-118.

Lee, J., et al.; "Experimental Evaluation of Silicone-Coated Dacron and Collagen Fabric-Film Laminate as Dural Substitutes," *Journal of Neurosurgery*, 1967, vol. 27, pp. 558-564.

Leong, K., et al., "Polyanhydrides for Controlled Release of Bioactive Agents," *Biomaterials*, 1986, vol. 7, pp. 364-371.

Leong, K., et al., "Polymeric Controlled Drug Delivery," *Advanced Drug Delivery Reviews*, 1987, vol. 1, pp. 199-233.

Maok, E., "Hemostatic Agents: Adjuncts to Control Bleeding," Today's O.R. Nurse, 1991, pp. 6-10.

Masar, B., et al., "Synthesis of Polyurethanes and Investigation of their Hydrolytic Stability," *Journal of Polymer Science: Polymer Symposium 66*, 1979, pp. 259-268.

Matsumoto, K., et al., "A Gelatin Coated Collagen-Polyglycolic Acid Composite Membrane as a Dural Substitute," *American Society for Artificial Internal Organs Journal*, 1992, vol. 47, pp. 641-645.

Maurer, P., et al. "Vicryl (Polyglactin 910) Mesh as a Dural Substitute," *Journal of Neurosurgery*, 1985, vol. 63, pp. 448-452.

McClure, J., et al., "Massive Gastroduodenal Hemorrhage: Treatment with Powdered Gelfoam and Buffered Thrombin Solution," *Surgery*, 1952, vol. 32, pp. 630-637.

McPherson, J., et al., "An Examination of the Biologic Response to Injectable, Glutaraldehyde Cross-linked Collagen Implants," *Journal of Biomedical Materials Research*, 1986, vol. 20, pp. 93-107.

McPherson, J. M., et al., "The Preparation and Physiochemical Characterization of an Injectable Form of Reconstituted, Glutaraldehyde Cross-linked, Bovine Corium Collagen," *Journal of Biomedical Materials Research*, 1986, vol. 20, pp. 79-92.

McPherson, J, et al., "The Effects of Heparin on the Physiochemical Properties of Reconstituted Collagen," *Collagen and Related Research*, 1988, vol. 1, pp. 65-82.

Meddings, N., et al., "Collagen Vicryl—A New Dural Prosthesis," *Acta Neurochirurgica*, 1992, vol. 117, pp. 53-58.

Mello, L., et al., "Duraplasty with Biosynthetic Cellulose: An Experimental Study," *Journal of Neurosurgery*, 1997, vol. 86, pp. 143-150.

Narotam, P., et al. "A Clinicopathological Study of Collagen Sponge as a Dural Graft in Neurosurgery," *Journal of Neurosurgery*, 1995, vol. 82, pp. 406-412.

Narotam, P., et al., "Experimental Evaluation of Collagen Sponge as a Dural Graft," *British Journal of Neurosurgery*, 1993, vol. 7, pp. 635-641.

Nimni, M., et al., "Chemically Modified Collagen: A Natural Biomaterial for Tissue Replacement," Journal of Biomedical Materials Researcy, 1987, vol. 21, pp. 741-771.

Nimni, M., "The Cross-Linking and Structure Modification of the Collagen Matrix in the Design of Cardiovascular Prosthesis," *Journal of Cardiac Surgery*, 1988, vol. 3, pp. 523-533.

O'Neill, P., et al., "Use of Porcine Dermis as a Dural Substitute in 72 Patients," *Journal of Neurosurgery*, 1984, vol. 61, pp. 351-354.

Palm, S., et al., "Dural Closure with Nonpenetrating Clips Prevents Meningoneural Adhesions: An Experimental Study in Dogs," *Neurosurgery*, 1999, vol. 45, No. 4, pp. 875-882.

Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," *Acta Neurochirurgica*, 1997, vol. 139, pp. 827-838.

Park, Y-K., et al., "Prevention of Arachnoiditis and Postoperative Tethering of the Spinal Cord with Gore-Tex Surgical Membrane: An Experimental Study with Rats," *Neurosurgery*, 1998, vol. 42, No. 4, pp. 813-824.

PCT International Preliminary Report on Patentability and Written Opinion mailed Feb. 17, 2009, International Application No. PCT/US2007/074984, 9 pages.

Pietrucha, K., "New Collagen Implant as Dural Substitute," *Biomaterials*, 1991, vol. 12, pp. 320-323.

Pitt, C., et al., "Biodegradable Drug Delivery Systems Based on Aliphatic Polyesters: Application to Contraceptives and Narcotic Antagonists," *Controlled Release of Bioactive Materials*, R. Baker, Ed., New York, Academic Press, 1980, pp. 19-43.

Porchet, F. et al., "Inhibition of Epidural Fibrosis with ADCON-L: Effect on Clinical Outcome One Year Following Re-operation for Recurrent Lumbar Radiculopathy," *Neurological Research*, 1999, vol. 21, pp. 551-560.

Raul, J.S., et al., "Utilisation du Polyester Urethane (NEUROPATCH®) Comme Substitut Dural," *Neurochirugie*, 2003, vol. 49, pp. 83-89, English abstract only on p. 83.

Reddy, M., et al., "A Clinical Study of a Fibrinogen-Based Collagen Fleece for Dural Repair in Neurosurgery," *Acta Neurochirurgica*, 2002, vol. 144, pp. 265-269.

Riley, S., et al., "Percutaneous Liver Biopsy with Plugging of Needle Track: A Safe Method for Use in Patients with Impaired Coagulation," *Lancet*, 1984, p. 436.

Rosenblatt, J., et al., "Effect of Electrostatic Forces on the Dynamic Rheological Properties of Injectable Collagen Biomaterials," *Biomaterials*, 1992, vol. 13, pp. 878-886.

Rosenblatt, J., et al., "Injectable Collagen as a pH-Sensitive Hydrogel," *Biomaterials*, 1994, vol. 12, pp. 985-995.

Ross, J., et al., "Association Between Peridural Scar and Recurrent Radicular Pain After Lumbar Discectomy: Magnetic Resonance Evaluation," *Neurosurgery*, 1996, pp. 855-863.

Rossler, B., et al., "Collagen Microparticles: Preparation and Properties," *Journal of Microencapsulation*, 1995, vol. 12, pp. 49-57.

San-Galli, F., et al., "Experimental Evaluation of a Collagen-Coated Vicryl Mesh as a Dural Substitute," *Neurosurgery*, 1992, vol. 30, pp. 396-401.

Shaffrey, C.I., et al., "Neurosurgical Applications of Fibrin Glue: Augmentation of Dural Closure in 134 Patients," *Neurosurgery*, 1990, vol. 26, pp. 207-210.

Sidman, K., et al., "Biodegradable, Implantable Sustained Release Systems Based on Glutamic Acid Copolymers" *Journal of Membrane Science*, 1979, vol. 7, pp. 227-291.

Smith, K., et al., "Delayed Postoperative Tethering of the Cervical Spinal Cord," *Journal of Neurosurgery*, 1994, vol. 81, pp. 196-201.

Springorum, H., "Die Verwendung von Kollagenfolien zur Uberbruckung von Defekten des Gleitgewebes bei Achillotenotomien und Achillessehnenrupturen," *Akt. Traumatol.*, 1985, vol. 15, pp. 120-121, English abstract only on p. 120.

Stricker, A., et al., "Die Verwendung von TissuFoil Membran bei der Sinusbodenaugmentation," *ellipse*, 2001, vol. 17, pp. 1-5, English abstract only on p. 1.

Sugitachi, A., et al., "A Newly Devised Chemo-Embolic Agent, G.T. XIII-ADM," *Gan. To. Kagaku Ryoho.*, 1985, vol. 12, pp. 1942-1943. English abstract retrieved from http://www.ncbi.nlm.nih.gov/ on Jan. 2, 2001.

Sugitachi, A., et al., "Locoregional Therapy in Patients with Malignant Pleural Effusion—Two Different Kinds of 'BAC Therapy'," *Gan. To. Kagaku Ryoho.*, 1992, vol. 19, pp. 1640-1643. English abstract retrieved from http://www.ncbi.nlm.nih.gov/ on Jan. 3, 2001.

Sugitachi, A., et al., "Preoperative Transcatheter Arterial Chemo-Embolization for Locally Advanced Breast Cancer: Application for New Thrombotic Materials," *Japanese Journal of Surgery*, 1983, vol. 13, pp. 456-458.

Kofidis, T., et al., "Clinically Established Hemostatis Scaffold (Tissue Fleece) as Biomatrix in Tissue-and Organ-Engineering Research," *Tissue Engineering*, 2003, vol. 9, pp. 517-523.

Baxter, "TissuFleece E Package Leaflet," Baxter International Inc., 2003, 4 pages, English portion of instructions for use.

Tobin, M., et al., "Plugged Liver Biopsy in Patients with Impaired Coagulation," *Digestive Diseases and Science*, 1989, vol. 34, pp. 13-15.

Tucker, H., *Absorbable Gelatin (Gelfoam) Sponge*, Springfiled, Illinois, Charles T. Thomas, 1965, pp. 3-125.

Vander Salm, T., et al., "Reduction of Sternal Infection by Application of Topical Vancomycin," *Journal of Thoracic and Cardiovascular Surgery*, 1989, vol. 98, pp. 618-622.

Vinas, F., et al., "Evaluation of Expanded Polytetrafluoroethylene (ePTFE) versus Polydioxanone (PDS) for the Repair of Dura Mater Defects," *Neurological Research*, 1999, vol. 21, pp. 262-268.

Wallace, D., et al., "Injectable Cross-Linked Collagen with Improved Flow Properties," *Journal of Biomedical Materials Research*, 1989, vol. 23, pp. 931-945.

Wallace, D., "The Relative Contribution of Electrostatic Interactions to Stabilization of Collagen Fibrils," *Biopolymers*, 1990, vol. 29, pp. 1015-1026.

Warren, W., et al., "Dural Repair Using Acellular Human Dermis: Experience with 200 Cases: Technique Assessment," *Neurosurgery*, 2000, vol. 46, pp. 1391-1396.

Yuki, N., et al., "Effects of Endoscopic Variceal Sclerotherapy Using GT XIII on Blood Coagulation Tests and the Renal Kallikrein-Kinin System," *Gastroentral. Japan*, 1990, vol. 25, pp. 561-567. English abstract retrieved from http://www.ncbi.nlm.nih.gov/ on Jan. 2, 2001.

Ziegelaar, B., et al., "The Characterisation of Human Respiratory Epithelial Cells Cultured on Resorbable Scaffolds: First Steps Towards a Tissue Engineered Tracheal Replacement," *Biomaterials*, 2002, vol. 23, pp. 1425-1438.

Ziegelaar, B., *Tissue Engineering of a Tracheal Equivalent*, Doctoral Thesis, Munich, Germany, Ludwig Maximilians University, 2004, 25 pages.

Zins, M., et al., "US-Guided Percutaneous Liver Biopsy with Plugging of the Needle Track: A Prospective Study in 72 High-Risk Patients," *Radiology*, 1992, vol. 184, pp. 841-843.

\* cited by examiner

FRAGMENTED POLYMERIC COMPOSITIONS AND METHODS FOR THEIR USE

CROSS REFERENCE TO RELATED APPLICATIONS

This application is a continuation of U.S. Ser. No. 13/174,963 filed Jul. 1, 2011, which is a continuation-in-part of U.S. Ser. No. 09/553,969 filed Apr. 21, 2000, which is a continuation of U.S. Ser. No. 09/032,370 filed Feb. 27, 1998 (now U.S. Pat. No. 6,066,325), which is a continuation-in-part of U.S. Ser. No. 08/903,674, filed on Jul. 31, 1997 (now U.S. Pat. No. 6,063,061), which claims the benefit of priority from U.S. 60/050,437 filed Jun. 18, 1997, and which is a continuation-in-part of U.S. Ser. No. 08/704,852 filed Aug. 27, 1996, U.S. Ser. No. 13/174,963 is also a continuation-in-part of U.S. Ser. No. 12/176,945 filed Jul. 21, 2008, which is a continuation of U.S. Ser. No. 09/908,464 filed Jul. 17, 2001. The full disclosures of each of these applications are incorporated herein by reference.

BACKGROUND OF THE INVENTION

Field of the Invention

The present invention relates generally to biocompatible cross-linked polymeric compositions and to the use of such compositions for the controlled delivery of aqueous agents to target sites.

It has long been recognized that tablets, capsules, and injections are not the optimum route of drug delivery for all purposes. These conventional routes often require frequent and repeated doses, resulting in a "peak and valley" pattern of therapeutic, agent concentration. Since each therapeutic agent has a therapeutic range above which it is toxic and below which it is ineffective, a fluctuating therapeutic agent concentration may cause alternating periods of ineffectiveness and toxicity. For this reason, a variety of "controlled release" drug formulations and devices have, been proposed for maintaining the therapeutic agent level within the desired therapeutic range for the duration of treatment. Using a polymeric carrier is one effective means to deliver the therapeutic agent locally and in a controlled fashion. In addition to controlled levels such systems often require less total drug and minimize systemic side effects.

Polymeric carriers may be biodegradable or non-biodegradable. For a non-biodegradable matrix, the steps leading to release of the therapeutic agent are water diffusion into the matrix, dissolution of the therapeutic agent, and out-diffusion of the therapeutic agent through the channels of the matrix. As a consequence, the mean residence time of the therapeutic agent existing in the soluble state is longer for a non-biodegradable matrix than for a biodegradable matrix where a long passage through the channels is no longer required. Since many pharmaceuticals have short half-lives, there is a significant chance that the therapeutic agent may be decomposed or inactivated inside the non-biodegradable matrix before it can be released. The risk is particularly significant for many biological macromolecules and smaller polypeptides, since these molecules are generally unstable in buffer and have low permeability through polymers. In fact, in a non-biodegradable matrix, many bio-macromolecules will aggregate and precipitate, clogging the channels necessary for diffusion out of the carrier matrix.

These concerns are largely alleviated by using a biodegradable controlled release matrix. Biodegradable polymers release contained drugs as the matrix is consumed or biodegraded during therapy. The polymer is usually selected to breakdown into subunits which are biocompatible with the surrounding tissue. The persistence of a biodegradable polymer in vivo depends on its molecular weight and degree of cross-linking, the higher the molecular weights and degrees of cross-linking resulting in a longer life. Common biodegradable polymers include polylactic acid (PLA, also referred to as polylactide), polyglycolic acid (PGA), copolymers of PLA and PGA, polyamides, and copolymers of polyamides and polyesters. PLA undergoes hydrolytic de-esterification to lactic acid, to normal product of muscle metabolism. PGA is chemically related to PLA and is commonly used for absorbable surgical sutures, as in the PLA/PGA copolymer. However, the use of PGA in controlled-release implants has been limited due to its low solubility in common solvents and subsequent difficulty in fabrication of devices.

An additional advantage of biodegradable drug delivery carriers is the elimination of the need for surgical removal after it has fulfilled its mission. Additional advantages include: 1) the ability to control release rate through variation of the matrix composition: 2) the ability to implant at sites difficult or impossible for retrieval; 3) an improved ability to deliver unstable therapeutic agents. This last point is of particular importance in light of the advances in molecular biology and genetic engineering which have lead to the commercial availability of many potent biological macromolecules. Such macromolecules usually have short in vivo half-lives and low GI tract absorption which often render them unsuitable tbr conventional oral or intravenous administration.

Ideally, a biodegradable therapeutic agent delivery system would simply consist of a solution, suspension, or dispersion of the drug in a polymer matrix. The therapeutic agent is released as the polymeric matrix decomposes, or biodegrades into soluble products which are excreted from the body. Unfortunately, the ability to design ideal biodegradable delivery systems is limited by many characteristics of the polymers, including weak mechanical strength, unfavorable degradation characteristics, toxicity, inflexibility, fabrication difficulty, and the like. Although known biodegradable polymers have a broad range of potential utility, there is no one single material available that could satisfy all requirements imposed by different applications. Accordingly, there continues to be need to develop new biodegradable polymers.

U.S. Pat. Nos. 5,672,336 and 5,196,185 describe a wound dressing comprising a micro-particulate fibrillar collagen having a particle size of 0.5-2.0 im. This composition generally comprises an aqueous phase and does not form a hydrogel as described in the present invention. U.S. Pat. No. 5,698,213 describes a cross-linked aliphatic poly-ester hydrogel useful as an absorbable surgical device and drug, delivery vehicle. U.S. Pat. No. 5,674,275 describes an acrylate or methacrylate based hydrogel adhesive. U.S. Pat. No. 5,306,501 describes a polyoxyalkylene based thermoreversible hydrogel useful as a drug delivery vehicle. U.S. Pat. Nos. 4,925,677 and 5,041,292 describe a hydrogel comprising a protein component cross-linked with a polysaccharide or mucopolysaccharide and useful as a drug delivery vehicle.

For these reasons, it would be desirable to provide improved compositions, methods, and kits for delivering biological macromolecule and other drugs to target body sites. In particular, it would be desirable to provide compositions which are compatible with a wide variety of drugs either in solution or in suspension, particularly drugs present in an aqueous carrier. Still more preferably, the compositions should be in the form of hydrogels which are biocompatible and which permit substantial control or "programming" of the release characteristics, including release rate, composition persistence, drug carrying capacity, product delivery characteristics (such as injectability), and the like. In addition to drug delivery and release, the products, methods, and kits of the present invention should be adaptable for localizing active agents at a target site, where the active agents can provide biological activity even prior to release from the product matrix. At least some of these objectives will be met by the embodiments of the invention described hereinafter.

Biodegradable injectable drug delivery polymers are described in U.S. Pat. No. 5,384,333 and by Jeong et al. (1997) "Nature," 388:860-862. Biodegradable hydrogels for controlled released drug delivery are described in U.S. Pat. No. 4,925,677, Resorbable collagen-based drug delivery systems are described in U.S. Pat. Nos. 4,347,234 and 4,291,013. Aminopolysaccharide-based biocompatible films for drug delivery are described in U.S. Pat. Nos. 5,300,494 and 4,946,870. Water soluble carriers for the delivery of taxol are described in U.S. Pat. No. 5,648,506.

Polymers have been used as carriers of therapeutic agents to effect a localized and sustained release (Langer, et al., Rev. Macro. Chem. Phys. C23(1), 61, 1983; Controlled Drug Delivery, Vol. I and II, Bruck, S. D. (ed.), CRC Press, Boca Raton: Fla, 1983; Leong et al., Adv. Drug Delivery Review, 1:199, 1987). These therapeutic agent delivery systems simulate infusion and offer the potential of enhanced therapeutic efficacy and reduced systemic toxicity.

Other classes of synthetic polymers which have been proposed for controlled release drug delivery include polyesters (Pitt, et al., in Controlled Release of Bioactive Materials, R. Baker, Ed., Academic Press, New York, 1980); polyamides (Sidman, et al., Journal of Membrane Science, 7:227, 1979); polyurethanes (Maser, et al., Journal of Polymer Science, Polymer Symposium, 66:259, 1979); polyorthoesters (Heller, et al., Polymer Engineering Science, 21:727, 1981); and polyanhydrides (Leong, et al., Biomaterials, 7:364, 1986).

Collagen-containing compositions which have been mechanically disrupted to alter their physical properties are described in U.S. Pat. Nos. 5,428,024; 5,352,715; and 5,204,382. These patents generally relate to fibrillar and insoluble collagens. An injectable collagen composition is described in U.S. Pat. No. 4,803,075. An injectable bone/cartilage composition is described in U.S. Pat. No. 5,516,532. A collagen-based delivery matrix comprising dry particles in the size range from 5 im to 850 im which may be suspended in water and which has a particular surface charge density is described in WO 96/39159. A collagen preparation having a particle size from 1 im to 50 im useful as an aerosol spray to form a wound dressing is described in U.S. Pat. No. 5,196,185. Other patents describing collagen compositions include U.S. Pat. Nos. 5,672,336 and 5,356,614.

A polymeric, non-erodible hydrogel that may be cross-linked and injected via a syringe is described in WO 96/06883.

The following pending applications, assigned to the assignee of the present application, contain related subject matter: U.S. Ser. No. 08/903,674, filed on Jul. 31, 1997; U.S. Ser. No. 60/050,437, filed on Jun. 18, 1997; U.S. Ser. No. 08/704,852, filed on Aug. 27, 1996; U.S. Ser. No. 08/673,710, filed Jun. 19, 1996: U.S. Ser. No. 60/011,898, filed Feb. 20, 1996; U.S. Ser. No. 60/006,321, filed on Nov. 7, 1996; U.S. Ser. No. 60/006,322, filed on Nov. 7, 1996; U.S. Ser. No. 60/006,324, filed on Nov. 7, 1996; and U.S. Ser. No. 08/481,712, filed on Jun. 7, 1995. The full disclosures of each of these applications is incorporated herein by reference.

SUMMARY OF THE INVENTION

The present invention provides improved biocompatible polymeric compositions and methods for applying such compositions at target sites in a patient's body. The methods and compositions will be particularly useful for delivering drugs and other active agents, such as biological macromolecules, polypeptides, oligopeptides, nucleic acids, small molecule drugs, and the like. The compositions will comprise biocompatible, cross-linked hydrogels, as described in more detail below, and the drug or other biologically active agent will typically be incorporated into the composition as art aqueous solution, suspension, dispersion, or the like. The drugs may be incorporated into the compositions prior to packaging, immediately prior to use, or even as the compositions are being applied to the target site. After introduction to the target site, the drug will usually be released over time as the composition degrades. In some instances, however, the drug or other biological agent may display activity while still incorporated or entrapped within the hydrogel. For example, the compositions and methods may find specific use in stopping or inhibiting bleeding (hemostasis), particularly when combined with a suitable hemostatic agent, such as thrombin, fibrinogen, clotting factors, and the like.

The compositions will have other uses as well, such as tissue supplementation, particularly for filling soft and hard tissue regions, including divots, tracts, body cavities, etc., present in muscle, skin, epithelial tissue, connective or supporting tissue, nerve tissue, ophthalmic and other sense organ tissue, vascular and cardiac tissue, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue. The compositions of the present invention will be still further useful for filling soil implantable devices, such as breast implants, where the material will be protected from cellular or enzyme degradation by a protective barrier or cover. The compositions will additionally be useful in other procedures where it is desirable to fill a confined space with a biocompatible and resorbable polymeric material. Additionally, the compositions may also find use for inhibiting the formation of tissue adhesions, such as spinal tissue adhesions, following surgery and traumatic injury.

The compositions of the present invention comprise a biocompatible, molecular cross-linked hydrogel. Usually the compositions will have substantially no free aqueous phase as defined herein below. The hydrogel is resorbable and fragmented, i.e. comprises small subunits having a size and other physical properties which enhance the flowability of the hydrogel (e.g. the ability to be extruded through a syringe) and the ability of the hydrogel to otherwise be applied onto and conform to sites on or in tissue, including tissue surfaces and defined cavities, e.g. intravertebral spaces, tissue divots, holes, pockets, and the like. In particular, the fragmented subunits are sized to permit them to flow when the compositions are subjected to stresses above a threshold level, for example when extruded through an orifice or cannula, when packed into a delivery site using a spatula, when sprayed onto the delivery site, or the like. The threshold stresses are typically in the range from $3 \times 10^4$ Pa to $5 \times 10^5$ Pa. The compositions, however, will remain generally immobile when subjected to stresses below the threshold level.

By "biocompatible," it is meant that the compositions will be suitable for delivery to and implantation within a human patient. In particular, the compositions will be non-toxic, non-inflammatory (or will display a limited inflammatory effect which is not inconsistent with their implantation), and be free from other adverse biological effects.

By "biodegradable," it is meant that the compositions will degrade and breakdown into smaller molecular subunits that will be resorbed and/or eliminated by the body over time, preferably within the time limits set forth below.

By "substantially free of an aqueous phase" it is meant that the compositions will be fully or partially hydrated, but will not be hydrated above their capacity to absorb water. In particular, a test for determining whether a composition has a free aqueous phase is set forth in Example 8 below. Hydrogels which are substantially free of an aqueous phase should release less than 10% by weight aqueous phase when subjected to a 10 lb. force in the test, preferably releasing less than 5% by weight, and more preferably less than 1% by weight, and more preferably releasing no discernable aqueous phase and displaying no collapse.

The compositions may be dry, partially hydrated or fully hydrated depending on the extent of hydration. The fully hydrated material will hold from about 400% to about 5000% water or aqueous buffer by weight, corresponding to a nominal increase in diameter or width of an individual particle of subunit in the range from approximately 50% to approximately 500%, usually from approximately 50% to approximately 250%. Thus, the size of particles in the dry powder starting material (prior to hydration) will determine the partially or fully hydrated size of the subunit (depending on the factors described below). Exemplary and preferred size ranges for the dry particles and fully hydrated subunits are as follows:

| Particle/Subunit Size | | |
| --- | --- | --- |
| | Exemplary Range | Preferred Range |
| Dry Particle | 0.01 mm-1.5 mm | 0.05 mm-1 mm |
| Fully Hydrated Hydrogel Subunit | 0.02 mm-3 mm | 0.1 mm-1.5 mm |

Compositions of the present invention will usually be in the form of a dry powder, a partially hydrated hydrogel, or a fully hydrated hydrogel. The dry powder (having a moisture content below 20% by weight) will be useful as a starting material for preparation of the hydrogels, as described below. The partially hydrated hydrogels are useful for applications where it is desired that the material further swell upon application to a moist target site, e.g. a tissue divot. The hilly hydrated forms will be useful for applications where in situ swelling is not desired, such as in the spinal column and other areas where nerves and other sensitive structures are present.

The dimensions of the subunits may be achieved in a variety of ways. For example, a cross-linked hydrogel having dimensions larger than the target range has defined below) may be mechanically disrupted at a variety of points during the production process. In particular, the composition may be disrupted (1) before or after cross-linking of a polymer starting material and (2) before or after hydration of the cross-linked or non-cross-linked polymer starting material, e.g. as a fully or partially hydrated material or as a dry particulate powder. The term "dry" will mean that the moisture content is sufficiently low, typically below 20% by weight water, so that the powder will be free-flowing and that the individual particles will not aggregate. The term "hydrated" will mean that the moisture content is sufficiently high, typically above 50% of the equilibrium hydration level, usually in the range from 70% to 95% of the equilibrium hydration level, so that the material will act as a hydrogel.

Mechanical disruption of the polymer material in the dr state is preferred in cases where it is desired to control the particle size and/or particle size distribution. It is easier to control comminution of the dry particles than the hydrated hydrogel materials, and the size of the resulting reduced particles is thus easier to adjust. Conversely, mechanical disruption of the hydrated, cross-linked hydrogels is generally simpler and involves fewer steps than does comminution of a dry polymer starting material. Thus, the disruption of hydrated hydrogels may be preferred when the ultimate hydrogel subunit size and/or size distribution is less critical.

In a first exemplary production process, a dry, non-cross-linked polymer starting material, e.g., dry gelatin powder, is mechanically disrupted by a conventional unit operation, such as homogenization, grinding, coacervation, milling, jet milling, and the like. The powder will be disrupted sufficiently to achieve dry particle sizes which produce hydrogel subunit sizes in the desired ranges when the product is partially or fully hydrated. The relationship between the dry particle size and the fully hydrated subunit size will depend on the swellability of the polymeric material, as defined further below.

Alternatively, a particulate polymeric starting material may be formed by spray drying. Spray drying processes rely on flowing a solution through a small orifice, such as a nozzle, to form droplets which are released into a counter-current or co-current gas stream, typically a heated gas stream. The gas evaporates solvent from the liquid starting material, which may be a solution, dispersion, or the like. Use of spray drying to form a dry powder starting material is an alternative to mechanical disruption of the starting material. The spray drying operation will usually produce a non-cross-linked dry powder product which is spherical in shape with a generally uniform particle size. The particles may then be cross-linked, as described below.

In many instances, the mechanical disruption operation can be controlled sufficiently to obtain both the particle size and particle size distribution within a desired range. In other cases, however, where more precise particle size distributions are required, the disrupted material can be further treated or selected to provide the desired particle size distribution, e.g. by sieving, aggregation, or the like. The mechanically disrupted polymeric starting material is then cross-linked as described in more detail below, and dried. The dried material may be the desired final product, where it may be rehydrated and swollen immediately prior to use. Alternatively, the mechanically disrupted, cross-linked material may be rehydrated, and the rehydrated material packaged for storage and subsequent use. Particular methods for packaging and using these materials are described below.

Where the subunit size of the fragmented hydrogel is less important, the dried polymeric starting material may be hydrated, dissolved, or suspended in a suitable buffer and cross-linked prior to mechanical disruption. Mechanical disruption of the pre-formed hydrogel will typically be achieved by passing the hydrogel through an orifice, where the size of the orifice and force of extrusion together determine the particle size and particle size distribution. While this method is often operationally simpler than the mechanical disruption of dry polymeric, particles prior to hydration and cross-linking, the ability to control the hydrogel particle size is much less precise.

In a particular aspect of the mechanical disruption of pre-formed hydrogels, the hydrogels may be packed in a syringe or other applicator prior to mechanical disruption. The materials will then be mechanically disrupted as they are applied through the syringe to the tissue target site, as discussed in more detail below. Alternatively, a non-disrupted, cross-linked polymeric material may be stored in a dry form prior to use. The dry material may then be loaded into a syringe or other suitable applicator, hydrated within the applicator, and mechanically disrupted as the material is delivered to the target site, again typically being through an orifice or small tubular lumen.

The polymer will be capable of being cross-linked and of being hydrated to form as hydrogel, as described in more detail below. Exemplary polymers include proteins selected from gelatin, collagen (e.g. soluble collagen), albumin, hemoglobin, fibrinogen, fibrin, fibronectin, elastin, keratin, laminin, casein and derivatives and combinations thereof. Alternatively, the polymer may comprise a polysaccharide, such as a glycosaminoglycan (e.g., hyaluronic acid or chondroitin sulfate), a starch derivative, a cellulose derivative, a hemicellulose derivative, xylan, agarose, alginate, chitosan, and combinations thereof. As a further alternative, the polymer may comprise a non-biologic hydrogel-forming polymer, such as polyacrylates, polymethacrylates, polyacrylamides, polyvinyl polymers, polylactide-glycosides, polycaprolactones, polyoxyethylenes, and derivatives and combinations thereof.

Cross-linking of the polymer may be achieved in any conventional manner. For example, in the case of proteins, cross-linking may be achieved using a suitable cross-linking agent, such as an aldehyde, sodium periodate, epoxy compounds, and the like. Alternatively, cross-linking may be induced by exposure to radiation, such as â-radiation or electron beam radiation. Polysaccharides and non-biologic polymers ma also be cross-linked using suitable cross-linking agents and radiation. Additionally, non-biologic polymers may be synthesized as cross-linked polymers and copolymers. For example, reactions between mono- and poly-unsaturated monomers can result in synthetic polymers having controlled degrees of cross-linking. Typically, the polymer molecules will each have a molecular weight in the range from 20 kD to 200 kD, and will have at least one link to another polymer molecule in the network, often having from 1 to 5 links, where the actual level of cross-linking is selected in part to provide a desired rate of biodegradability in the ranges set forth below.

The extent of cross-linking of the polymer has an effect on several functional properties of the hydrogel including extrudability, adsorptiveness of surrounding biological fluids, cohesiveness, ability to fill space, swelling ability and ability to adhere to the tissue site. The extent of cross-linking of the polymeric hydrogel composition may be controlled by adjusting the concentration of cross-linking agent, controlling exposure to cross-linking radiation, changing the relative amounts of mono- and poly-unsaturated monomers, varying reaction conditions, and the like. Typically, the degree of cross-linking is controlled by adjusting the concentration of cross-linking agent.

Exposure to radiation, such as â-radiation, may also be carried out in order to sterilize the compositions before or after packaging. When the compositions are composed of radiation-sensitive materials, it will be necessary to protect the compositions from the undesirable effects of sterilizing radiation. For example, in some cases, it will be desirable to add a stabilizer, such as ascorbic acid, in order to inhibit degradation and/or further excessive cross-linking of the materials by free radical mechanisms.

The hydrogel compositions of the present invention will typically have a solids content in the range from 1% by weight to 70% by weight. Optionally, the compositions may comprise at least one plasticizer as described in more detail below. Suitable plasticizers include polyethylene glycols, sorbitol, glycerol, and the like.

The equilibrium swell of the cross-linked polymers of the present invention may range from 400% to 5000%, 400% to 3000%, 400% to 2000%, usually ranging from 400% to 1300%, preferably being from 500% to 1100%, depending on its intended use. Such equilibrium swell may be controlled by varying the degree of cross-linking, which in turn is achieved by varying the cross-linking conditions, such as the type of cross-linking method, duration of exposure of a cross-linking agent, concentration of a cross-linking agent, cross-linking temperature, and the like.

Gelatin-containing hydrogels having equilibrium swell, values from about 400% to 1300% were prepared and are described in the Experimental section hereinafter. It was found that materials having differing equilibrium swell values perform differently in different applications. For example, the ability to inhibit bleeding in a liver divot model was most readily achieved with cross-linked gelatin materials having a swell in the range from 600% to 950%, often from 700% to 950%. For a femoral artery plug, lower equilibrium swell values in the range from 300% to 600% were more successful. Thus, the ability to control cross-linking and equilibrium swell allows the compositions of the present invention to be optimized for a variety of uses.

In addition to equilibrium swell, it is also important to control the hydration of the material immediately prior to delivery to a target site. Hydration is defined as the percentage of water contained by the hydrogel compared to that contained by the hydrogel when its fully saturated, that is, at its equilibrium swell. A material with 0% hydration will be non-swollen. A material with 100% hydration will be at its equilibrium water content and fully swollen. Hydrations between 0% and 100% will correspond to swelling between the minimum and maximum amounts. As a practical matter, many dry, non-swollen materials according to the present invention will have some residual moisture content, usually below 20% by weight, more usually from 8% to 15% by weight. When the term "dry" is used herein, it will specify materials having a low moisture content, usually below 20%, often below 10%, and frequently below 5% by weight, where the individual particles are free flowing and generally non-swollen.

Hydration can be adjusted very simply by controlling the amount of aqueous buffer added to a dry or partially hydrated cross-linked material prior to use. Usually, at a minimum, it will be desirable to introduce sufficient aqueous buffer to permit extrusion through a syringe or other delivery device. In other cases, however, it may be desirable to utilize a spatula or other applicator for delivering less fluid materials. The intended use will also help determine the desired degree of hydration. In eases where it is desired to fill or seal a moist cavity, it is generally desirable to employ a partially hydrated hydrogel which can swell and fill the cavity by absorbing moisture from the target site. Conversely, fully or substantially fully hydrated hydrogels are preferred for application in the brain, near the spine, and to target sites near nerves and other sensitive body structures which could be damaged by post-placement swelling. It would also be possible to prepare the hydrogel compositions of the present invention with excess buffer, resulting, in a two-phase composition having a fully hydrated hydrogel and a free buffer phase.

A preferred hydrogel material according to the present invention is a gelatin which has been cross-linked to achieve from 600% to 950%, usually 700% to 950% swell at equilibrium hydration. The material will be disrupted to have a hydrogel particle size in the range from 0.01 mm to 1.75 mm, preferably 0.05 mm to 1.0 mm, often 0.05 mm to 0.75 mm, and frequently between 0.05 mm and 0.5 mm, and will preferably be hydrated at a level sufficient to achieve 70% to 100% of the equilibrium swell prior to application to the site.

In some cases, the hydrogel compositions of the present invention may contain a combination of two or more different materials, e.g. combinations of proteins and polysaccharides and/or non-biologic polymers, as well as combinations of two or more individual materials from each of the polymer types, e.g. two or more proteins, polysaccharides, etc.

The polymeric compositions of the present invention may also comprise combinations of the disrupted, cross-linked polymer hydrogels described above and non-cross-linked polymeric materials. The disrupted, cross-linked polymeric hydrogels consist of a plurality of subunits having a size determined by preparation method. The size is selected to be useful for packing a confined volume, having both the flowability and the rate of biodegradability described in the Experimental section below. The discrete nature of the cross-linked, subunits, however, will leave void areas which may be filled by combination with a non-cross-linked polymeric material. The non-cross-linked polymeric or other filler material may comprise an of the polymeric materials listed above, and may optionally but not necessarily be the same polymeric material which has been cross-linked to form the cross-linked mechanically disrupted hydrogel. The relative amounts of cross-linked polymer and non-cross-linked polymer may vary, typically having a weight ratio in the range from 20:1 to 1:1 (cross-linked polymer:non-cross-linked polymer), usually in the range from 10:1 to 2:1, preferably from 5:1 to 2:1.

The hydrogels of the present application may be applied using a syringe, a spatula, a brush, a spray, manually by pressure, or by any other conventional technique. Usually, the hydrogels will be applied using a syringe or similar applicator capable of extruding the hydrogel through an orifice, aperture, needle, tube, or other passage to form a bead, layer, or similar portion of material. Mechanical disruption of the hydrogels can occur as the hydrogel is extruded through an orifice in the syringe or other applicator, typically having a size in the range from 0.01 mm to 5.0 mm, preferably 0.5 mm to 2.5 mm. Preferably, however, the polymeric hydrogel will be initially prepared from a powder having, a desired particle size (which upon hydration yields hydrogel subunits of the requisite size) or will be partially or entirely mechanically disrupted to the requisite size prior to a final extrusion or other application step.

The compositions may be applied at varying degrees of hydration, usually but not necessarily being at least partially hydrated. If applied in a non-hydrated form, the compositions will swell to their full equilibrium swell value, i.e. from about 400% to about 5000% as set forth above. When applied at their full hydration, the compositions will display substantially equilibrium hydration and little or no swelling when applied to tissue. Swelling of the non-hydrated and partially hydrated compositions results from absorption of moisture from the tissue and surroundings to which the composition is being applied.

The present invention still further provides kits comprising any of the hydrated or non-hydrated hydrogel materials described above in combination with written instructions for use (IFU) which set forth any of the methods described above for applying the hydrogel onto a target site on tissue. The composition and written instructions will be included together in a conventional container, such as a box, jar, pouch, tray, or the like. The written instructions may be printed on a separate sheet of paper or other material and packaged on or within the container or may be printed on the container itself. Usually, the composition(s) will be provided in a separate sterile bottle, jar, vial, or the like. When the hydrogel material is non-hydrated, the kit may optionally include a separate container with a suitable aqueous buffer for hydration. Other system components such as the applicator, e.g. syringe, may also be provided.

The FloSeal® product is a hemostatic composition and is available in a package including two syringes. A first syringe is filled with granules of cross-linked bovine gelatin which are pre-hydrated with a buffer solution. The gelatin hydrogel contains about 85% (w/w) water and is in the form of a flowable hydrogel. Immediately prior to use in the operating room, thrombin in aqueous saline is mixed with the gelatin hydrogel. The thrombin is prepared in saline and drawn up in a second syringe, and the syringes are connected together permitting mixing of thrombin and the gelatin.

The resulting mixture of the gelatin hydrogel granules and the thrombin has been found to be a highly effective hemostatic sealant when applied to a bleeding site. Typically, the sealant will be applied through the syringe in which it has been mixed to the bleeding site. Blood will percolate through the resulting bed of hydrogel granules, and the thrombin reacts with fibrinogen in the blood to form a fibrin clot around the gelatin to seal the bleeding site.

The FloSeal® product is described in Hood et al., *Efficacy of Topical Hemostat FloSeal™ in Vascular Surgery*, an Abstract funded by Fusion Medical Technologies, Inc. which was publicly presented in September 1999. Patents covering the FloSeal® product include U.S. Pat. Nos. 6,063,061 and 6,066,325. A dual syringe system suitable for mixing and delivering a collagen, gelatin, or other collagen-derived component and a thrombin component of the FloSeal™ product is described in U.S. Pat. No. 5,908,054. The complete disclosures of each of these patent references is hereby incorporated by reference.

A fluid dispersion and delivery assembly includes first and second delivery devices, typically syringes, coupled by a fluid transfer assembly. The delivery devices each include a port or access opening in fluid communication with the interior of the delivery device. The access openings are selectively fluidly coupled by the fluid transfer assembly.

The fluid transfer assembly includes a body having, a central bore within which a hollow tube reciprocally passes. The hollow tube has first and second ends which are situated within the interiors of the first and second delivery devices. Openings at the ends of the tube permit fluid to be transferred from the interior of the first delivery device to the interior of the second delivery device.

The first delivery device can be prefilled with the fluid. Tn some situations, such as when the delivery devices are syringes and the fluid has a short shelf-life, it may be desirable to fill the first syringe with the fluid just prior to use. In such an event the fluid transfer assembly can be first mounted to the access opening of the first syringe. The plunger is depressed to cause the tube to extend from the fitting. The second end of the tube can then be placed in a reservoir or other container holding the fluid. The piston is then moved from its depressed position to its retracted position to create a partial vacuum within the second syringe; because the second end of the tube remains immersed in the fluid, the fluid is drawn up into the interior of the first syringe. At this point the second end of the tube preferably remains exposed and extends a short distance from the fitting.

The second syringe is then mounted to the fitting with the second end of the tube extending just into the interior of the second syringe. The fluid in the first syringe can be evenly dispersed into the material in the second syringe by depressing the first plunger; doing so causes the second end of the tube to pass through the material within the second syringe as the fluid is evenly dispersed into the second syringe through the opening or openings at the second end of the tube. After the fluid is dispersed into the material in the second syringe, the fluid transfer assembly can be removed from the second syringe and the combined material can be dispensed from the second syringe directly or with the aid of an additional delivery element.

The fitting is preferably a double Luer fitting to permit the fitting to be mounted to conventional syringes. If the delivery device, is other than a conventional syringe, the fitting can be modified accordingly.

One of the primary advantages of the invention is that it permits a fluid, such as a hemostatic solution, to be evenly dispersed into a material, such as a flowable gel material, in a simple and convenient fashion. The use of conventional syringes as the delivery devices helps to reduce the cost of the system.

The present invention finds particular utility when used to disperse a diluent, such as a hemostatic solution, into a flowable gel material. Such materials can be used in filling tissue divots, tissue tracks, body cavities, surgical defects and the like to inhibit post-surgical spinal and other tissue adhesions. An example of such a material is disclosed in U.S. patent application Ser. No. 08/704,852 filed Aug. 27, 1996.

DESCRIPTION OF THE SPECIFIC EMBODIMENTS

Figure 1:
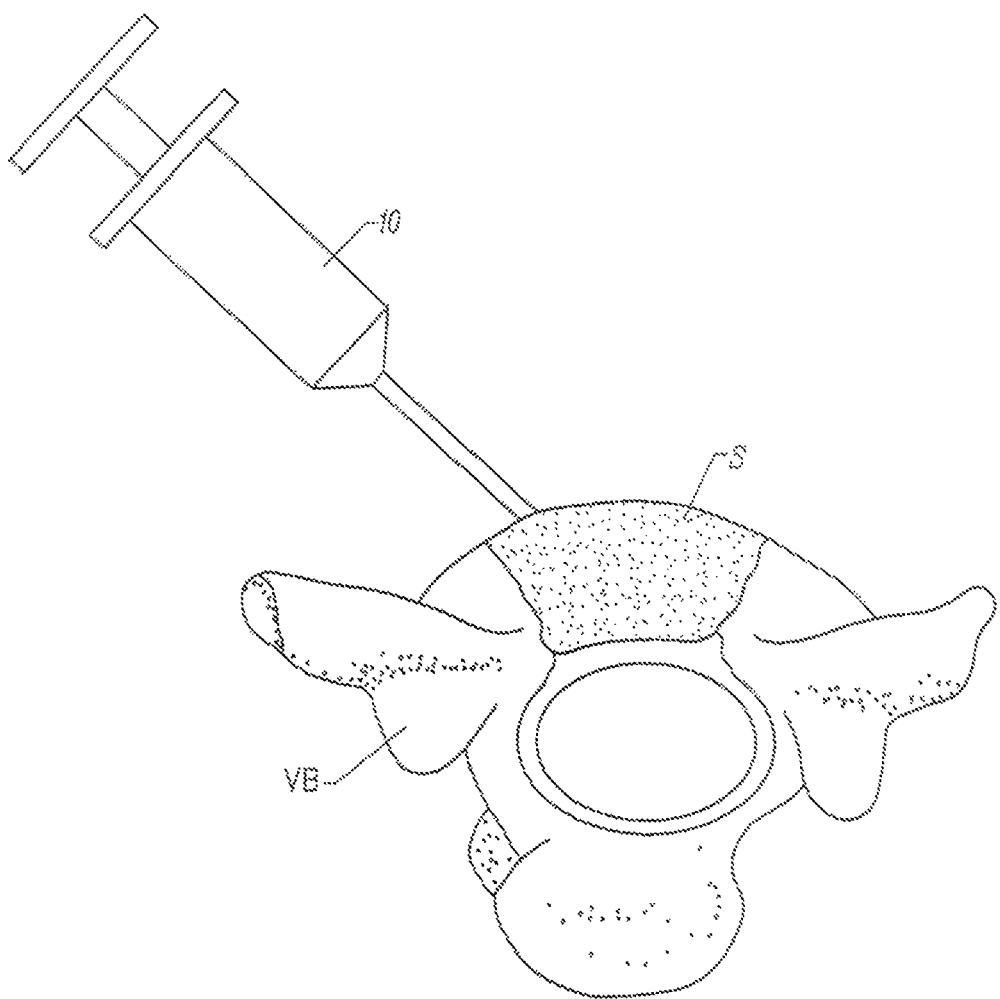
FIG. 1 illustrates the application of the molecular cross-linked polymeric hydrogel of the present invention to a surgically created defect in the vertebral body for preventing post-surgical spinal adhesions.

Compositions according to the present invention comprise resorbable biocompatible molecular cross-linked hydrogels. By "biocompatible" is meant that the materials will meet the criteria in standard # ISO 10993-1 (International Organization for Standardization, Geneva, Switzerland). By "resorbable," it is meant that the compositions will degrade or solubilize, when placed directly into a target sire in a patients body (and not protected within an implant device such as a breast implant), over a time period of less than one year, usually from 1 day to 120 days. A particular protocol for measuring resorption and degradation is set forth in the Experimental section hereinafter. By "molecular cross-linked", it is meant that the materials comprise polymer molecules (i.e. individual chains) which are attached by bridges composed of either an element, a group, or a compound, where the backbone atoms of the polymer molecules are joined by chemical bonds. Cross-linking may be effected in a variety of ways, as will be described in greater detail below.

By "hydrogel," it is meant that the composition comprises a single phase aqueous colloid in which a biologic or non-biologic polymer, as defined in more detail below, absorbs water or an aqueous buffer. The hydrogel comprises multiple sub-networks, where each sub-network is a molecular cross-linked hydrogel having dimensions which depend on the degree of hydration and are within the ranges set firth above. Preferably, the hydrogels will have little or no free water, i.e. water cannot be removed from the hydrogel by simple filtration.

By "percent swell," it is meant that the dry weight is subtracted from the wet weight, divided by the dry weight and multiplied by 100, where wet weight is measured after the wetting agent has been removed as completely as possible from the exterior of the material, e.g. by filtration, and where dry weight is measured after exposure to an elevated temperature for a time sufficient to evaporate the wetting agent, e.g., 2 hours at 120*C.

"Equilibrium swell" is defined as the percent swell at equilibrium after the polymeric material has been immersed in a wetting agent for a time period sufficient for water content to become constant, typically 18 to 24 hours.

"Target site" is the location to which the hydrogel material is to be delivered. Usually, the target site will be the tissue location of interest, but in some cases the hydrogel may be administered or dispensed to a location near the location of interest, e.g. when the material swells in situ to cover the location of interest.

The hydrogels of the present invention may be formed from biologic and non-biologic polymers, Suitable biologic polymers include proteins, such as gelatin, soluble collagen, albumin, hemoglobin, casein, fibrinogen, fibrin, fibronectin, elastin, keratin, laminin, and derivatives and combinations thereof. Particularly preferred is the use of gelatin or soluble non-fibrillar collagen, more preferably gelatin, and exemplary gelatin formulations are set forth below. Other suitable biologic polymers include polysaccharides, such as glycosaminoglycans (e.g. hyaluronic acid and chondroitin sulfate), starch derivatives, xylan, cellulose derivatives, hemicellulose derivatives, agarose, alginate, chitosan, and derivatives and combinations thereof. Suitable non-biologic polymers will be selected to be degradable by either of two mechanisms, i.e. (1) break down of the polymeric backbone or (2) degradation of side chains which result in aqueous solubility. Exemplary nonbiologic hydrogel-forming polymers include synthetics, such as polyacrylates, polymethacrylates, polyacrylamides, polyvinyl resins, polylactide-glycosides, polycaprolactones, polyoxyethylenes, and derivatives and combinations thereof.

The polymer molecules may be cross-linked in any manner suitable to form an aqueous hydrogel according to the present invention. For example, polymeric molecules may be cross-linked using bi- or poly-functional cross-linking agents which covalently attach to two or more polymer molecules chains. Exemplary bifunctional cross-linking agents include aldehydes, epoxies, succinimides, carbodiimides, maleimides, azides, carbonates, isocyanates, divinyl sulfuric, alcohols, amines, imidates, anhydrides, halides, silanes, diazoacetate, aziridines, and the like. Alternatively, cross-linking may be achieved by using, oxidizers and other agents, such as periodates, which activate side-chains or moieties on the polymer so that they may react with other side-chains or moieties to form the cross-linking bonds. An additional method of cross-linking comprises exposing the polymers to radiation, such as gamma radiation, to activate the side polymer to permit cross-linking, reactions. Dehydrothermal cross-linking methods are also suitable. Dehydrothermal cross-linking of gelatin can be achieved by holding it at an elevated temperature, typically 120° C., for a period of at least 8 hours. Increasing the extent of cross-linking, as manifested in a decline in percent swell at equilibrium, can be achieved by elevating the holding temperature, extending the duration of the holding time, or a combination of both. Operating under reduced pressure can accelerate the cross-linking reaction. Preferred methods for cross-linking gelatin molecules are described below.

Optionally, the molecular cross-linked hydrogel may include a plasticizer to increase the malleability, flexibility, and rate of degradation of the hydrogel. The plasticizer may be an alcohol, such as polyethylene glycol, sorbitol, or glycerol, preferably being polyethylene glycol having a molecular weight ranging from about 200 to 1000 D, preferably being about 400 D. The plasticizers will be present in the compositions at from about 0.1% of the solids by weight to about 30% of the solids by weight, preferably from 1% of the solids by weight to 5% of the solids by weight of the composition. The plasticizers are particularly beneficial for use with hydrogels having a high solids content, typically above 10% by weight of the composition (without plasticizer).

Exemplary methods for producing molecular cross-linked, gelatins are as follows. Gelatin is obtained and placed in an aqueous buffer to form a non-cross-linked hydrogel, typically having a solids content from 1% to 70% by weight, usually from 3% to 10% by weight. The gelatin is cross-linked, typically by exposure to either glutaraldehyde (e.g. 0.01% to 0.05% w/w, overnight at 0° to 15° C. in aqueous buffer), sodium periodate (e.g. 0.05 M, held at 0° C. to 15° C. for 48 hours) or 1-ethyl-3-(3-dimethylaminopropyl) carbodiimide ("EDC") (e.g., 0.5% to 1.5% w/w, overnight at room temperature), or by exposure to about 0.3 to 3 mudguards of gamma or electron beam radiation. Alternatively, gelatin particles can be suspended in an alcohol, preferably methyl alcohol or ethyl alcohol, at a solids content of 1% to 70% by weight, usually 3% to 10% by weight, and cross-linked by exposure to a cross-linking agent, typically glutaraldehyde (e.g., 0.01% to 0.1% w/w, overnight at room temperature). In the case of aldehydes, the pH should be held from about 6 to 11, preferably from 7 to 10. When cross-linking with glutaraldehyde, the cross-links are formed via Schiff bases which may be stabilized by subsequent reduction, e.g. by treatment with sodium borohydride. After cross-linking, the resulting granules may be washed in water and optionally rinsed in an alcohol, dried and resuspended to a desired degree of hydration in an aqueous medium having a desired buffer and pH. The resulting hydrogels may then be loaded into the applicators of the present invention, as described in more detail hereinafter. Alternatively, the hydrogels may be mechanically disrupted prior to or after cross-linking, also as described in more detail hereinafter.

Exemplary methods for producing molecular cross-linked gelatin compositions having equilibrium percent swells in the range from about 400% to about 1300%, preferably 600% to 950%, are as follows. Gelatin is obtained and placed in an aqueous buffer (typically at a pH of 6 to 11, preferably at a pH between 7 and 10) containing a cross-linking agent in solution (typically glutaraldehyde, preferably at a concentration of 0.01% to 0.1% w/w) to form a hydrogel, typically having, a solids content from 1% to 70% by weight, usually from 3% to 10% by weight. The hydrogel is well mixed and held overnight at 0-15° C. as cross-linking takes place. It is then rinsed three times with deionized water, twice with an alcohol (preferably methyl alcohol, ethyl alcohol, or isopropyl alcohol) and allowed to dry at room temperature. Optionally, the hydrogel may be treated with sodium borohydride to further stabilize the cross-linking.

The compositions of the present invention may be further combined with other materials and components, such as bioactive component(s) to be delivered to the patient, viscosity modifiers, such as carbohydrates and alcohols, and other materials intended for other purposes, such as to control the rate of resorption. Exemplary bioactive components include, but are not limited to, proteins, carbohydrates, nucleic acids, and inorganic and organic biologically active molecules such as enzymes, antibiotics, antineoplastic agents, bacteriostatic agents, bacteriocidal agents, antiviral agents, hemostatic agents, local anesthetics, anti-inflammatory agents, hormones, antiangiogenic agents, antibodies, neurotransmitters, psychoactive drugs, drugs affecting reproductive organs and oligonucleotides, such as antisense oligonucleotides. Such bioactive components will typically be present at relatively low concentrations, typically below 10% by weight of the compositions, usually below 5% by weight, and often below 1% by weight. Two or more of such active agents may be combined in a single composition and/or two or more compositions may be used to deliver different active components where said components may interact at the delivery site.

Exemplary hemostatic agents include thrombin, fibrinogen and dotting factors. Hemostatic agents like thrombin may be added in concentrations ranging from 50 to 10,000 Units thrombin per ml hydrogel, preferably from about 100 Units thrombin per ml hydrogel to about 1000 Units thrombin per ml hydrogel.

The molecular cross-linked hydrogels of the present invention can be mechanically disrupted at the time they are delivered to a target site by extrusion through an orifice or other flow restriction, or they can be mechanically disrupted in a batch process prior to delivery to a target site. The primary purpose of this mechanical disruption step is to create multiple subunits of hydrogel having a size which enhances the ability to fill and pack the space to which it is being delivered. Another purpose of the mechanical disruption is to facilitate passage of the hydrogel down small diameter tubes, cannulas, and/or other applicators to the target site. Without mechanical disruption, the molecular cross-linked hydrogels will have difficulty conforming to and filling the irregularly target spaces which are being treated, e.g. intravertebral spaces in the spinal column, tissue divots, percutaneous tissue tracks, and the like. By breaking the hydrogel down to smaller sized sub-units, such spaces can be filled much more efficiently while retaining the mechanical integrity and persistence of the cross-linked hydrogel which are essential for it to act as an anti-adhesive agent, tissue tiller, or the like. Surprisingly, it has been found that a single manual extrusion of the composition, typically using a syringe having an orifice in size in the range from 0.01 mm to 5.0 mm, preferably from 0.1 mm to 2.5 mm, provides the proper amount of mechanical disruption to enhance the hydrogel properties as described above.

Alternatively, the hydrogel compositions of the present invention may be mechanically disrupted prior to their final use or delivery, Molecular cross-linking of the polymer chains of the hydrogel can be performed before or after its mechanical disruption. The hydrogels may be mechanically disrupted in batch operations, such as mixing, so long as the hydrogel composition is broken down into sub-units having a size in the 0.01 mm to 5.0 mm range set forth above. When the hydrogel composition is disrupted prior to use, the hydrogel can be applied or administered by techniques other than extrusion e.g., using a spatula, spoon, or the like. Other batch mechanical disruption processes include pumping through a homogenizer or mixer or through a pump which compresses, stretches, or shears the hydrogel to a level which exceeds a fractural yield stress of the hydrogel. In some cases, extrusion of the polymeric composition causes the hydrogel to be converted from a substantially continuous network, i.e. a network which spans the dimensions of the original hydrogel mass, to a collection of sub-networks or sub-units having dimensions in the ranges set forth above. In other cases it may be desirable to partially disrupt the hydrogel compositions prior to packaging in the syringe or other applicator. In such cases, the hydrogel material will achieve the desired sub-unit size prior to final extrusion.

In a presently preferred embodiment, the polymer may be initially prepared (e.g. by spray drying) and/or be mechanically disrupted prior to being cross-linked, often usually prior to hydration to form a hydrogel. The polymer may be provided as a finely divided or powdered dry solid which may be disrupted by further commination to provide particles having a desired size, usually being narrowly confined within a small range. Further size selection and modification steps, such as sieving, cyclone classification, etc., may also be performed. For the exemplary gelatin materials described hereinafter, the dry particle size is preferably in the range from 0.01 mm to 1.5 mm, more preferably from 0.05 mm to 1.0 mm. An exemplary particle size distribution will be such that greater than 95% by weight of the particles are in the range from 0.05 mm to 0.7 min. Methods for comminuting the polymeric starting material include homogenization, grinding, coacervation, milling, jet milling, and the like. Powdered polymeric starting materials may also be formed by spray drying. The particle size distribution may be further controlled and refined by conventional techniques such as sieving, aggregation, further grinding, and the like.

The dry powdered solid may then be suspended in an aqueous buffer, as described elsewhere herein, and cross-linked. In other cases, the polymer may be suspended in an aqueous buffer, cross-linked, and then dried. The cross-linked, dried polymer may then be disrupted, and the disrupted material subsequently resuspend in an aqueous buffer. In all the cases, the resulting material comprises a cross-linked hydrogel having discrete sub-networks having the dimensions set forth above.

The compositions of the present invention, after mechanical disruption, will be resorbable, i.e., they will biodegrade in the patient's body, in a period of less than one year, usually from 1 to 120 days, preferably from 1 to 90 days, and more preferably from 2 to 30 days following their initial application. This is particularly true when the materials are used for preventing post-surgical and other adhesions, where a barrier is necessary between the healing tissue surfaces only for so long as the tissue is healing. Techniques for measuring the length of time required for resorption are set forth in Example 11 in the Experimental section below. In other cases, such as when the compositions are contained within an implantable device, such as a breast implant, resorption of the material will be prevented by the membrane or other mechanical barrier surrounding the compositions (unless the integrity of the barrier is broken).

Referring now to FIG. 1, a method for preventing adhesions following a laminectomy procedure will be described. A syringe 10 containing the resorbable molecular cross-linked hydrogel of the present invention is used to apply the hydrogel in such a manner that all exposed dura is covered. Usually, the hydrogel will be resorbed over a time period in the range from 7 to 60 days.

Figure 2A:
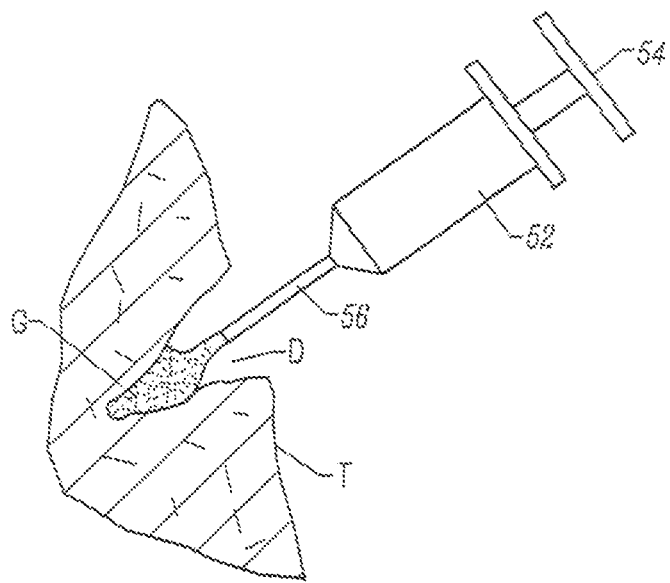
FIGS. 2A and 2B illustrate application of the molecular cross-linked polymeric hydrogel compositions of the present invention to a detect in soft tissue, where the treated region is optionally covered with a protective patch after the defect is filled with the polymeric composition.
Figure 2B:
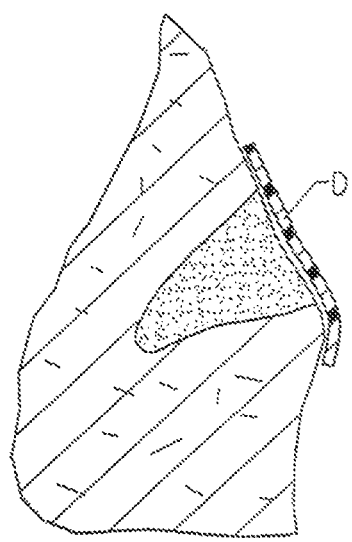

Referring now to FIGS. 2A and 2B, the molecular cross-linked hydrogels of the present invention may also be used to fill divots D in soft tissue T. A syringe 50 comprising a barrel 52, plunger 54 and cannula 56 contains the molecular cross-linked hydrogel in the interior of the barrel 52. The hydrogel G is extruded through the cannula 56 by depressing the plunger 54 in a conventional manner. Sufficient hydrogel is extruded to fill the divot, as shown in FIG. 2B. Preferably, a partially hydrated hydrogel which will swell further upon exposure to the moist tissue environment will be used. It may be desirable to place a patch P over the exposed surface of the hydrogel, as shown in FIG. 2B. The patch may be an adhesive or other conventional self-securing patch. Preferably, however, the patch comprises a collagen, gelatin, or other film that may be immobilized by applying energy e.g. optical or radio frequency energy as described in published PCT applications WO 96/07355 and WO 92/14513.

Figure 3A:
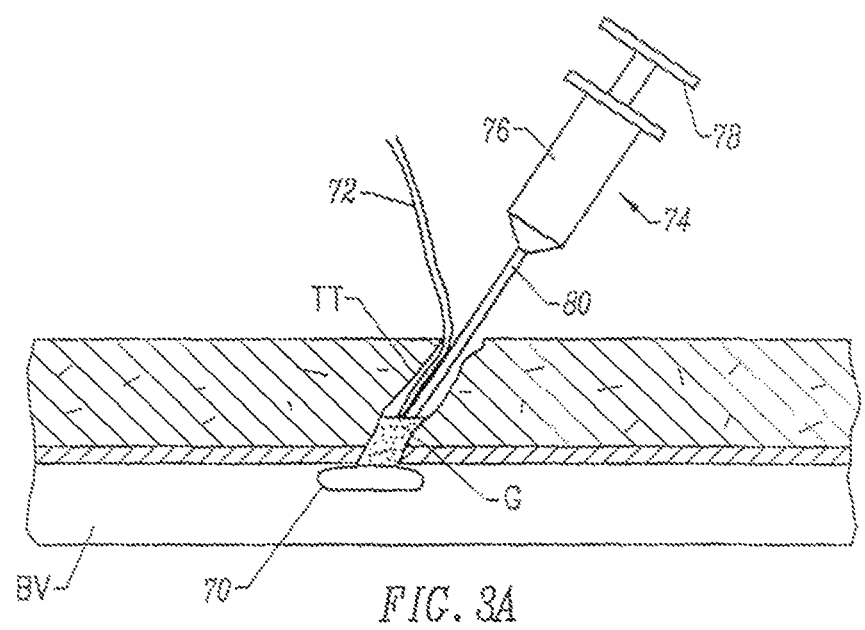
FIGS. 3A and 3B illustrate use of the molecular cross-linked polymeric compositions of the present invention for filling a percutaneous tissue penetration to a blood vessel, such as a tissue tract formed as part of an intravascular catheterization procedure.
Figure 3B:
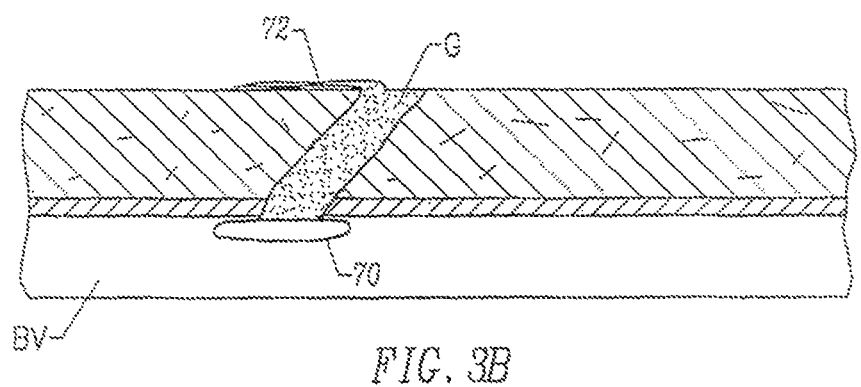

Referring now to FIGS. 3A and 3B, compositions and methods of the present invention may also be used to fill percutaneous tissue tracts TT which were formed through overlying tissue to access blood vessels BV. A barrier element 70 may be placed along the inner wall of the blood vessel at the distal end of the tissue tract TT. Filament 72 may be used to hold the barrier element 70 in place. A syringe 74 comprising a barrel 76, plunger 78, and cannula 80 is then used to extrude the molecular cross-linked hydrogel material, of the present invention into the tissue tract over the harrier element 70. The hydrogel G will be used to fill the entire interior volume of the tissue tract TT, as shown in FIG. 3B, and will preferably be partially hydrated to permit post-placement swelling as described above. Optionally, a patch or other cover may be placed over the exposed surface of the tissue tract (not shown). The barrier element 70 may then be removed.

Figure 4:
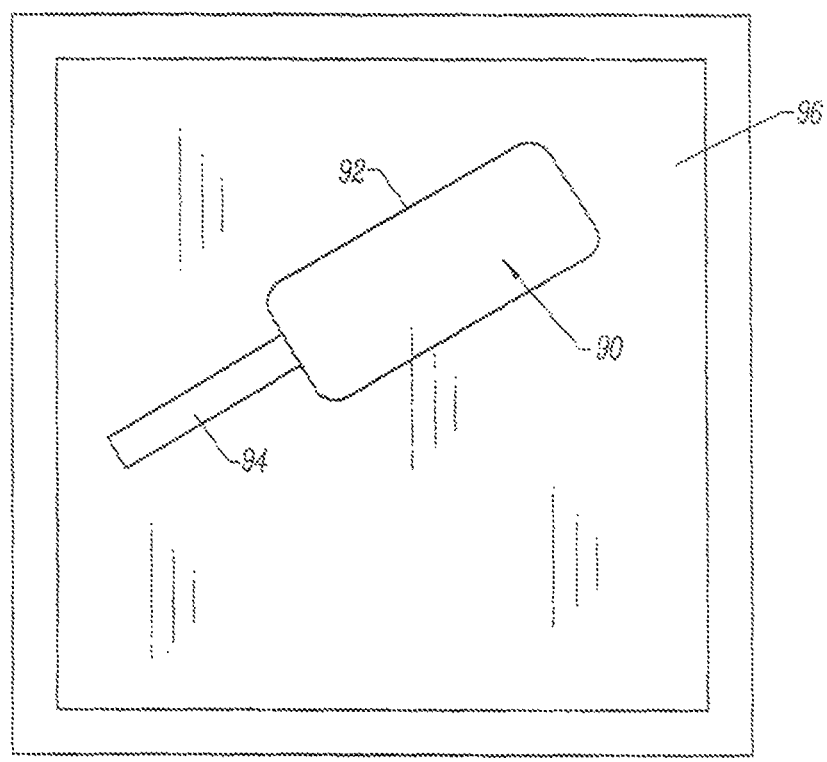
FIG. 4 illustrates a kit comprising a sterile package for an applicator containing the molecular cross-linked polymeric composition of the present invention.
Figure 5:
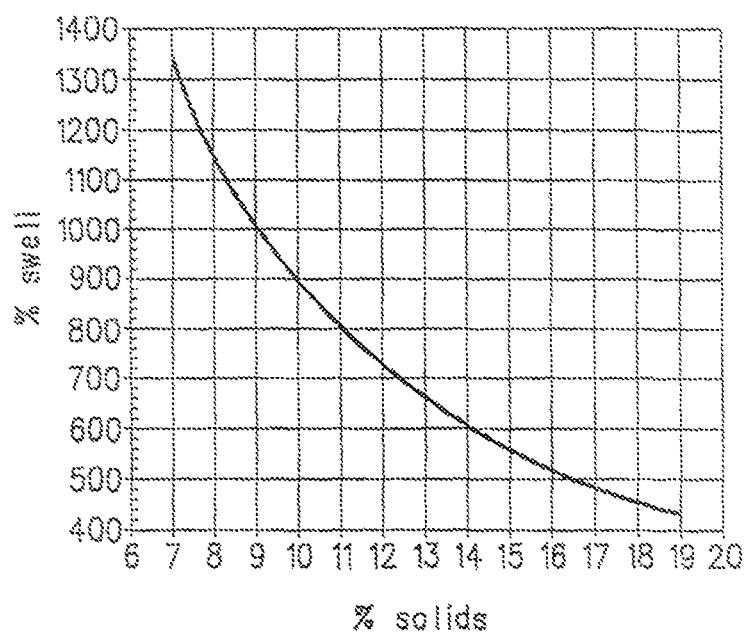
FIG. 5 illustrates the correlation between percent swell and the percent solids of the polymeric hydrogel.
Figure 6:
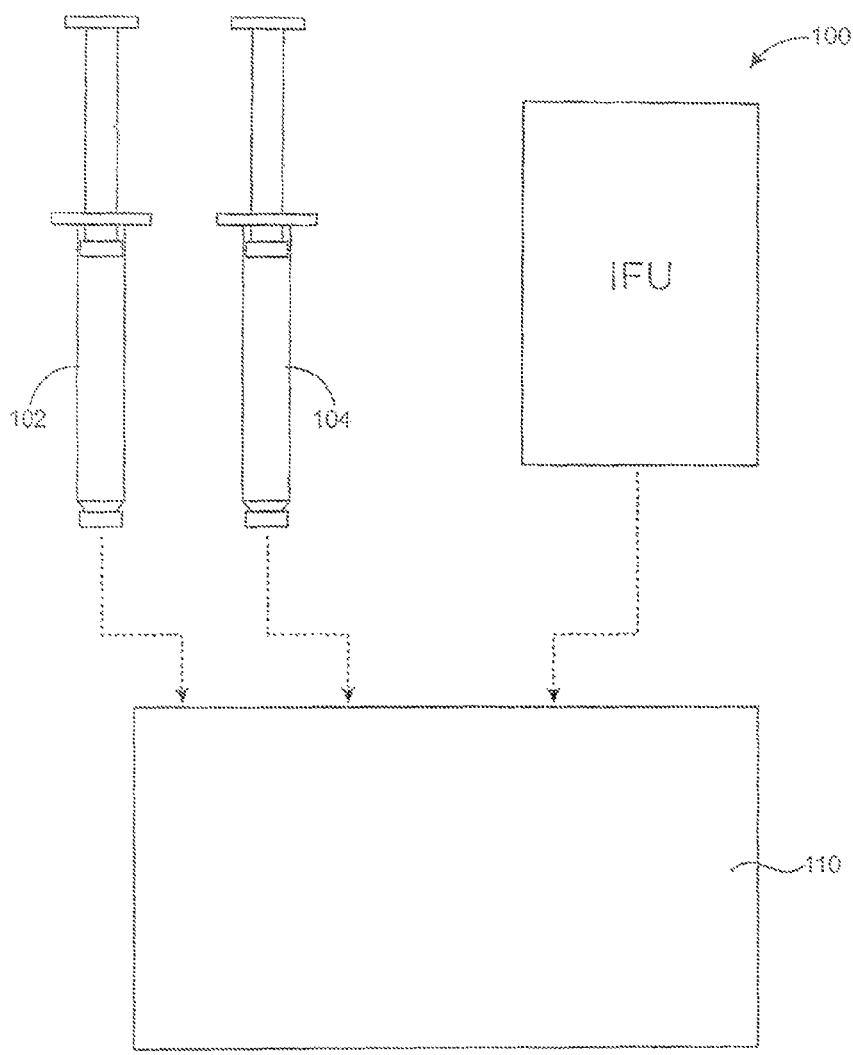
FIG. 6 illustrates a kit constructed in accordance with the principles of the present invention.

Referring now to FIG. 4, the present invention comprises kits including the hydrated, partially hydrated, and/or non-hydrated polymeric compositions described above packaged in a suitable container, usually with written instructions for use. For example, the composition may be packaged in an applicator 90 which contains the pre-extruded molecular cross-linked hydrogel of the present invention. The applicator may take a wide variety of forms, including syringes as previously described, in FIG. 4, the applicator 90 comprises a tube 92 having a neck 94 which defines an extrusion orifice. The hydrogel is contained within the tube and may be extruded through the neck 94 by squeezing the tube. The applicator 90 is preferably contained in a sterile package 96. The sterile package may take a variety of forms, and is illustrated as an envelope comprising a backing sheet and a clear plastic cover. Such packages may be sterilized in a conventional manner. Optionally, the radiation used to cross-link the hydrogel may also be used to sterilize the entire package. The instructions for use may be printed on the packaging or provided on a separate sheet placed in the package.

The present invention may also be used to inhibit bleeding (cause hemostasis) on an abraded or damaged tissue surface, e.g., any organ surface including the liver, spleen, heart, kidney, intestine, blood vessels, vascular organs, and the like. A syringe containing the resorbable molecular cross-linked hydrogel combined with a hemostasis agent is used to apply the hydrogel to the abraded or damaged tissue site. The hydrogel is applied so that the actively bleeding abraded or damaged area is completely covered with the resorbable molecular cross-linked hydrogel. Suitable hemostatic agents include thrombin, fibrinogen, and other clotting factors, as described for example in U.S. Pat. Nos. 5,411,885; 4,627,879; 4,265,233; 4,298,598; 4,362,567; 4,377.572; and 4,442,655, the disclosures of which are incorporated, herein by reference. Conveniently, catalytic components of the hemostasis agent, e.g. thrombin, may be combined in the syringe immediately prior to use so that their combined activities are preserved until applied to the tissue.

When used in regions surrounding nerves and other sensitive body structures, it is preferable to employ fully hydrated hydrogels (i.e. with >95% of hydration at equilibrium swell) in order to avoid damage to the nerves from swelling in an enclosed environment.

The following examples are offered by way of illustration, not by way of limitation.

EXPERIMENTAL

Example 1

Materials and Methods for Production of a Fragmented Polymeric Product

Fragmented polymeric compositions are generally prepared as follows:

Using pyrogen-free glassware and distilled water throughout, food grade gelatin (300 Bloom, Atlantic Gelatin, General Foods Corp., Woburn, Mass.) at 10% solids was allowed to swell in 0.1 N aq. sodium hydroxide, and 0.05 sodium periodate and held at 0° C. to 8° C. for 2-3 days. The swollen granules were washed in distilled water until the pH reached 8. The neutralized swollen granules were dried in a laminar flow hood and re-suspended in 0.05 M sodium phosphate, 0.15 M sodium chloride, pH 7.2+/−0.2, at 10% solids. The composition was then loaded into 3.0 cc syringes and irradiated at 3.0 megarad with electron beam to sterilize.

Example 2

Materials and Methods for Production of a Fragmented Polymeric Product

Gelatin (300 Bloom, Atlantic Gelatin, General Foods Corp., Woburn, Mass.) was allowed to well in an aqueous buffer (e.g. 0.05 M sodium phosphate, 0.15 M sodium chloride, pH 7.2+/−0.2) at 1-10% solids and was cross-linked by either glutaraldehyde (0.01-0.05%, w/w overnight, room temperature), by sodium periodate (0.05 M, to 8° C., 48 hours) or by 0.3-3.0 megarads of gamma or electron beam irradiation. The hydrogels were then extruded from a syringe using normal manual pressure.

Example 3

Materials and Methods for Production of a Fragmented Polymeric Product

Gelatin (300 Bloom, Atlantic Gelatin, General Foods Corp., Woburn, Mass.) was allowed to swell in distilled water at 1-10% solids (w/w) chilled to 5° C. The resultant hydrogel was fragmented by stirring with an impeller driven by a motor. Then, sodium periodate and sodium hydroxide were added and mixed to achieve 0.05 M sodium periodate and 0.10 M sodium hydroxide. The chilled mixture was held at 0° C. to 8° C. for 2-3 days. The cross-linked hydrogel fragments were then washed with 5° C. water to achieve pH 8. Finally the hydrogel fragments were washed with an aqueous buffer (e.g., 0.05 sodium phosphate and 0.15 sodium chloride, pH 7.2+/−0 2) and left at 0° C. to 8° C. to equilibrate with the buffer. Free buffer was decanted from the fragmented hydrogel mass and the hydrogel particles were loaded into syringes and irradiated at 3.0 megarads by electron beam or gamma irradiation to sterilize. Such sterilized fragmented were then extruded directly from the syringe causing further fragmentation.

Example 4

Biocompatibility in Rabbit Model

The test material was prepared by mixing 0.5 mL of sterile saline for injection with 5 mL of the fragmented gelatin composition as follows: The saline solution was injected into the fragmented gelatin composition contained in a 5 cc syringe through a dispersion needle embedded in the fragmented gelatin composition. One mL aliquots of the fragmented gelatin composition were transferred into 1 cc syringe and a 14 gauge needle was attached. The entire assembly was weighed. Following administration of the test article, the syringe and needle assembly were re-weighed to determine the mass of the dosed compound.

A total of 14 rabbits were included in this study. All procedures were performed aseptically. Rabbits were clipped free of fur over the para vertebral muscles. The test material was delivered from a 1 mL syringe with a 14 gauge needle. The needle attached to the syringe containing the test article was inserted into the muscle at a 45° angle. An approximate 0.2 mL portion of the test material was injected into the muscle and needle withdrawn. A total of four test sites were implanted in the right paravertebral muscle of each rabbit. Additionally, a USP negative control strip was implanted as a marker approximately 2-3 mm away from each test site, distal to the vertebral column as compared to the test article. In the opposite (left) muscle, four USP negative control sections were implanted similarly as performed for the markers.

Observations included daily health checks, adverse reactions related to implantation, morbidity and mortality. Body weights were recorded prior to implantation, at monthly intervals, and at termination. At each of the harvest times post-implantation; 2, 4, 6 and 13 weeks, 3 rabbits were euthanized. A gross examination for irritation at each implant site was performed. The paravertebral muscles were dissected free and fixed in 10% neutral buffered formalin. Following appropriate embedding, sectioning and staining, the muscles were evaluated microscopically for evidence of irritation, presence or absence of test article and relative degree of resorption of the implanted test article.

All animals appeared clinically normal throughout the study and gained appropriate weights during the course of the study. At 2 weeks, the inflammatory reaction around the injected test material was localized, with very little extension of this inflammation observed beyond the test material. At four weeks, the inflammatory reaction around the injected test material was localized, with very little extension of this inflammation observed beyond the test material. At four weeks, there was a minimal to mild inflammatory and fibrotic reaction observed at the test sites, which resolved to a minimal reaction at six weeks. By thirteen weeks the inflammatory response was characterized as extremely minimal. The test material was considered to be a non-irritant, compared to the USP negative control material at six and thirteen weeks post implantation.

Example 5

Vessel Plug

This study demonstrated the effectiveness of the fragmented polymeric composition to seal a vessel puncture. The femoral artery of a farm grade Hampshire/Yorkshire cross pig (Pork Power Farms, Turlock, Calif.) was identified and cannulated using a needle (SmartNeedle™, CardioVascular Dynamics, Irvine, Calif.). After the guide wire was placed, a 9 French dilator was used to create a runnel to the vessel and enlarge the femoral artery opening. The dilator was removed and a 7 French sheath was introduced into the femoral artery. The guide wire was then removed. Positioning was checked by withdrawing blood into the sheath side arm. Pulsatile arterial bleeding was also observed at the point of insertion of sheath at the skin incision. As the sheath was removed, a 18 gauge Teflon catheter tip attached to a hypodermic syringe was used to introduce the fragmented gelatin composition of Example 1 into the tunnel. No bleeding, was observed at the point of exit demonstrating the effectiveness of the fragmented gelatin composition in sealing the vessel puncture site and surrounding tissue.

Example 6

Fragmented Polymeric Composition as a Carrier

This study demonstrated the effectiveness of the fragmented polymeric composition of Example 1 as a carrier to fill and seal a tissue divot in the liver. Three wounds (2 tissue divots and 1 tissue puncture) were induced in the liver of a farm grade Hampshire/Yorkshire cross pig (Pork Power Farms, Turlock, Calif.).

Liver tissue divot #1 was actively bleeding following the surgical creation of a tissue divot. A syringe, containing approximately 1 ml of fragmented gelatin composition containing approximately 500 U of thrombin (500 to 1000 units/ml) was extruded from a syringe and applied to completely fill the tissue defect. After 2-3 minutes, a blood clot formed causing immediate cessation of bleeding. When the applied composition was grasped with forceps, it appeared to adhere quite well to the tissue and had good integrity. The sealant was manually challenged and no additional bleeding was observed.

Liver tissue divot #2 was actively bleeding following the surgical creation of a tissue divot. Approximately 1 ml of fragmented gelatin composition containing thrombin (approximately 500 units/ml) was extruded from a syringe and applied to completely fill the tissue defect. A Rapiseal™ patch (Fusion Medical Technologies, Inc., Mountain View, Calif.) was applied over the filled defect using an argon beam coagulator (Valleylab, Boulder, Colo., or Birtcher Medical Systems, Irvine, Calif.). Immediate cessation of bleeding occurred.

Liver puncture #1, was actively bleeding following the surgical creation of a blunt puncture. Approximately 0.8 ml of fragmented gelatin composition containing thrombin (approximately 500 units/ml) was extruded from a syringe and applied to completely fill the tissue defect. Approximately 2 minutes following the delivery of the fragmented gelatin composition, all bleeding stopped.

Spleen puncture #1 was actively bleeding, following the surgical creation of a blunt puncture, Approximately 0.8 ml of fragmented gelatin composition containing thrombin (approximately 500 units/ml) was extruded from a syringe and applied to completely fill the tissue defect. Approximately 2 minutes following the delivery of the fragmented gelatin composition, all bleeding stopped.

in the above four examples, the delivery system used was a 3 cc syringe (Becton Dickinson, Franklin Lakes, N.J.). It contained the fragmented gelatin composition of example 1.

A material according to the present invention for filling tissue divots and other defects could be prepared as follows. A thrombin solution (0.5 ml 4,000 to 10,000 U/ml) is added to 4.5 ml of flowable hydrogel to produce 5 ml of hydrogel containing 400 to 1000 U/ml thrombin. The hydrogel can be used in any convenient amount, e.g. 0.5 ml to 5 ml.

Example 7

Fragmented Polymeric Composition as a Tissue Filler and Anastomic Sealant

This study demonstrated the effectiveness of the fragmented gelatin composition as a wound closure system that fills and seals tissue defects. Four tissue divots were surgically induced, 1 in the lung, 2 in the liver and 1 in the spleen of a farm grade Hampshire/Yorkshire cross pig (Pork Power Farms, Turlock, Calif.).

On the lung, following the surgical creation of the tissue divot, an air leak was Observed. Approximately 1 ml of the fragmented gelatin composition of Example 1 was extruded from a syringe and applied to completely fill the tissue defect, A Rapiseal™ patch (Fusion Medical Technologies, Inc., Mountain View, Calif.) was applied using an argon beam coagulator (Valleylab, Boulder, Colo., or Birtcher Medical Systems, Irvine, Calif.). Immediate cessation of the air leak occurred. When the applied patch was grasped with forceps, it appeared to adhere quite well to the tissue and had good integrity. The fragmented gelatin composition was challenged by ventilating the lung to a pressure of 28 cm water. No air leak was observed.

On the liver, following the surgical creation of the tissue divot, excessive bleeding was observed. Approximately 1 ml of fragmented gelatin composition was extruded from a syringe and applied to completely fill the tissue defect. The fragmented composition swelled and adequately stopped the bleeding although some seepage bleeding was observed.

On the liver, following the surgical creation of the tissue divot, excessive bleeding was observed, Approximately 1 ml of fragmented gelatin composition was extruded from a syringe and applied to completely fill the tissue defect. A Rapiseal™ patch (Fusion Medical Technologies, Inc., Mountain View, Calif.) was applied using an argon beam coagulator (Valleylab, Boulder, Colo., or Birtcher Medical Systems, Irvine, Calif.). Immediate cessation of the bleeding occurred. When the applied patch was grasped with forceps, it appeared to adhere quite well to the tissue and had good integrity.

Spleen puncture #1 was actively bleeding following the surgical creation of a blunt puncture. Approximately 0.8 ml of fragmented gelatin composition was extruded from a syringe and applied to completely fill the tissue defect. Approximately 2 minutes following the delivery of the fragmented gelatin composition, all bleeding, stopped.

A female juvenile farm grade goat (Clovertop Dairy, Madera, Calif.) was used under appropriate anesthesia. The right carotid artery was exposed. The vessel was carefully dissected to remove any connective tissue. The vessel was clamped using atraumatic vascular clamps, separated by a distance of approximately 2-3 cm. The vessel was dissected using a standard scalpel blade to expose 2 free vessels ends. An end-to-end anastomosis was created using 6-0 prolene suture in an interrupted fashion. Following completion of the anastomoses, the clamps were released. Bleeding was observed at the anastomotic site. Approximately 2 cc of the fragmented gelatin composition containing thrombin (approximately 500 units/ml) was extruded from a syringe around the anastomoses. Gauze was placed against the composition. Approximately 3 minutes after the application of the fragmented gelatin composition, all bleeding was observed to have ceased. The incision was appropriately closed and the animal was allowed to recover for subsequent follow-up.

Example 8

Materials and Methods for Determining Force Necessary to Release Aqueous Phase

Two disks were cut from a filter mesh of sufficient pore size to retain the sample under test. The disks were of approximately the same diameter as the inside of the barrel of a 5 ml syringe (Becton Dickinson, Franklin Lakes, N.J.). The plunger was removed from the 5 ml syringe and the two mesh disks were inserted and pushed into place with the plunger. The plunger was replaced and the syringe placed into an assembly allowing, the syringe plunger to be depressed by the force gauge of a Chatillon TCD 200 Test Stand (Chatillon, Greensboro, N.C.). The force required to cause the release of aqueous phase from the test material was then determined.

A 51 μm stainless steel mesh was used to retain the test materials. The application of 50 lbs. force to 2 ml of the material of Example 4 (above) mixed with reconstituted thrombin (Thrombin-JMI™, GenTrac, Inc., Middelton, Wis.) according to the package insert was insufficient to cause the release of any free liquid. nor any noticeable collapse of the material.

A sterile absorbable gelatin sponge (2.5 ml; Gelfoam®, the UpJohn Co., Kalamazoo, Mich.) was soaked in reconstituted thrombin (Thrombin-JMI™, GenTrac, Inc., Middelton, Wis.) according to the package insert and inserted into the same apparatus as above. The application of less than 1 lb. of pressure caused the release of almost all of the aqueous phase and the collapse of the Gelfoam material to approximately 0.5 mL.

Example 9

Materials and Methods of Ascorbate Addition to Hydrogel Prior to Irradiation

Gelatin particles (300 Bloom, Atlantic Gelatin, General Foods Corp. Woburn, Mass.) were suspended at 5%-15% by weight in methyl alcohol (Aldrich, Milwaukee, Wis.) containing 0.01%-0.1% by weight glutaraldehyde (Sigma, St. Louis, Mo.) and stirred overnight at ambient temperature. Alternatively, gelatin particles, obtained from an extract of calf hide (Spears Co., PA) were suspended at 5%-15% by weight in aqueous buffer at pH 9 containing 0.01%-0.1% by weight glutaraldehyde (Sigma) to form a hydrogel that was well-mixed and refrigerated overnight. The cross-linked gelatin fragments were then rinsed three times with alcohol and dried at ambient temperature. Equilibrium swelling for the rinsed, cross-linked, gelatin was then measured, and 0.5 g-1.0 g portions of this material were packed into 5 cc syringes. 3.0 ml-4.5 ml of aqueous buffer containing ascorbic acid or a salt of ascorbic acid, e.g. 0.02 M sodium phosphate (1.1. Baker. Phillipsburg, New jersey), 0.15 M sodium chloride (VWR, West Chester, Pa.), 0.005 M sodium ascorbate (Aldrich), pH 7.0, was added to the syringes containing cross-linked gelatin using a second syringe and a three-way stopcock, with care taken not to introduce extraneous air into the syringes, to form a hydrogel within several syringes. Alternatively, an aqueous buffer that did not contain ascorbic acid or a salt of ascorbic acid but was otherwise of similar composition and pH was added to other syringes containing crosslinked gelatin to form a hydrogel within them. The hydrogel-containing syringes were then gamma-irradiated under refrigerated conditions at 3.0±0.3 megarads. Equilibrium swell was measured for the hydrogel contained within the syringes after irradiation. Hydrogels that were formed using buffers that contained ascorbic acid or a salt of ascorbic acid generally maintained values for equilibrium swell upon irradiation within ±20%, and usually ±10%, of the value prior to irradiation, while hydrogels that were formed using buffers not containing ascorbic acid or a salt of ascorbic acid experienced a decrease in equilibrium swell of 25-30% of its value prior to irradiation.

Example 10

Materials and Methods of Cross-Linking Measuring Percent Swell

Gelatin particles were allowed to swell in an aqueous buffer (e.g., 0.2 M sodium phosphate, pH 9.2) containing a cross-linking agent (e.g., 0.005-0.5% by weight glutaraldehyde). The reaction mixture was held refrigerated overnight and then rinsed three times with deionized water, twice with ethyl alcohol, and allowed to dry at ambient temperature. The dried, cross-linked gelatin was resuspended in an aqueous buffer at a low solids concentration (2-3%) at ambient temperature for a fixed period of time. Buffer Was in substantial excess of the concentration needed for equilibrium swelling, and two phases (a hydrogel phase and a buffer) were present. The suspension containing wet hydrogel was then filtered by applying vacuum on a 0.8 im nominal cut-off filter membrane (Millipore, Bedford, Mass.). After removal of extraneous buffer, the combined weight of the retained wet hydrogel and wet filter membrane was recorded. The hydrogel and membrane were then dried at approximately 120° C. for at least two hours, and the combined weight of the dried hydrogel residue and dried filter membrane was recorded. Several measurements of samples of wet filter membrane without hydrogel residue and dried filter membrane without hydrogel were also performed and were used to deduce the net weight of wet hydrogel and dry hydrogel. "Percent swell" was then calculated as follows:

$$\text{percent swell} = 100 \times \frac{(\text{wet weight of hydrogel} - \text{dry weight of hydrogel})}{\text{dry weight of hydrogel}}$$

Swell measurements were conducted at least in triplicate and averaged for a given sample of gelatin. The value of percent swell for samples resuspended in buffer for 18-24 hr prior to measuring wet weight was defined as "equilibrium swell."

The resulting cross-linked gelatin materials displayed equilibrium swell values in the range from 400% to 1300%. The degree of equilibrium swell depended on the method and extent of cross-linking.

Example 11

Degradation

Thirty rabbits (15 untreated control animals and 15 animals treated with fragmented gelatin composition) underwent surgery to mimic splenic injury and bleeding. A lesion on the spleen was created by making a controlled wound with a 6 mm biopsy punch. In the "Treated" group, the experimentally created injury was immediately treated with the fragmented gelatin composition to cause hemostasis of the wound. "Control" group animals were not treated during the first 7.5 minutes to demonstrate the amount of bleeding resulting from the lesion. At 7.5 minutes from the time the injury was caused, the fragmented gelatin composition was then used to stop bleeding from the lesion to prevent spontaneous exsanguination and death of the animal. All animals were allowed to recover. Ten animals each were euthanized on Days 14 and 28 post-surgery. The final necropsy date for the remaining animals was determined alter the Day 28 animals were evaluated. In animals harvested at the Day 28 time point it was difficult to determine via gross examination if the test material was present or not, therefore half of the remaining animals were harvested at Day 42 and the other half at Day 56. At the time of necropsy, the site of the splenic lesion and the peritoneal cavity were evaluated macroscopically. Presence of fragmented gelatin composition in the peritoneal cavity away from the site of placement was noted and evaluated, as well as its presence or absence at the splenic lesion. The presence or absence of postoperative adhesions at the site of the splenic lesion was also evaluated and noted. The spleen was carefully dissected and processed for histological evaluation of biocompatibility and biodegradation.

The application of the fragmented gelatin composition to the surgically created wounds on the spleen resulted in good hemostatic tamponade. Following application of the fragmented gelatin composition at the time of surgery, rabbits were survived for 14, 28, 42, and 56 days postoperatively. One rabbit died of unrelated pneumonia at Day 5 postoperatively and the spleen was not harvested for histopathological examination.

At necropsy, the site of the splenic lesion as well as the peritoneal cavity in general were evaluated grossly. Presence of the fragmented gelatin composition in the peritoneal cavity away from the site of placement was evaluated, as well as the presence or absence of the fragmented gelatin composition at the splenic lesion. The presence or absence of adhesions at the site of the splenic lesion were evaluated and noted. The spleen was carefully dissected and processed for histological evaluation.

Grossly, the site of the splenic lesion was visible in all animals, at all time points. Macroscopically, the fragmented gelatin composition was absent in two of the ten Day 14 animals. At all other time points it was not possible to identify the fragmented gelatin composition macroscopically. The macroscopic absence of the hydrogel material as measured in this rabbit model defines the degradation of the hydrogel as that term is used herein and in the claims.

In three of ten animals sacrificed at 14 days postoperatively, small amounts of the fragmented gelatin composition were found free-floating in the abdominal cavity. This most likely represents the excess material that had migrated from its placement site at the splenic lesion. In no case where this material was found away from the splenic lesion was there any evidence of tissue reaction front the visceral surfaces or the omentum. No material was found away from the site of the splenic lesion in animals that were harvested at any other time point.

No postoperative adhesions associated with the fragmented gelatin composition material were noted at the site of the splenic lesion in any animal. In all animals, as expected, there was omentum attached to the site of the splenic lesion.

Other adhesions involving the spleen were rare, and when noted were incidental and usually associated with the incision of the body wall.

The fragmented gelatin composition was absent macroscopically and microscopically in two of the ten animals from the 14 day time point. At 28 days post-implant, the fragmented gelatin composition was not visible on moss observation and microscopically was completely absent in five out of ten rabbits examined and present in minimal amounts in the remaining animals, showing that the fragmented gelatin composition. was composition was essentially biodegraded by 28 days. The fragmented gelatin composition was completely absent in all five animals examined at 42 days post-implant and was found in minimal amounts in only one of four rabbits examined at 56 days post-implant. Healing, of the splenic wound was proceeding in a normal fashion at Day 42 and more so at Day 56.

Example 12

Fragmented Polymeric Product Composed of Gelatin Cross-Linked Using EDC

Gelatin (Atlantic Gelatin, General Foods Corp., Woburn, Mass.) was allowed to dissolve in distilled water at 1-10% solids (w/w) (more preferably at 8%) at 70° C. 1-Ethyl-3-(3-dimethylaminopropyl) carbodiimide (EDC) (Sigma, St. Louis. MO) at 0.2%-3.5% (more preferably 0.2%-0.3%) was then added. The resultant hydrogel formed on stirring was left at room temperature for one hour. The hydrogel was dried using a Freezone 12 freeze dry system, (Labconco, Mo.) and ground finely using a Waring Blender model No, 31BC91 (VWR, Willard, Ohio). The dried polymeric composition was then loaded into syringes and equilibrated with buffer. The equilibrium swell was determined to be at least 1000% according to the method described in Example 10. The results are shown in Table 1,

TABLE 1

| Gelatin (mg) | EDC | Swell (%) |
|---|---|---|
| 500 (8%) | 13.5 mg (0.25%) | 1080 |
| 500 (8%) | 13.5 mg (0.25%) | 1126 |
| 100 (7.4%) | 0.945 mg (0.35%) | 1620 |
| 100 (7.4%) | 9.45 mg (3.5%) | 1777 |

Example 12

Fragmented Polymeric Product Composed of Gelatin and Poly(L)Glutamic Acid, Cross-Linked Using EDC Gelatin (Atlantic Gelatin, General Foods Corp., Woburn: MA) was allowed to dissolve in distilled water at 1-10% solids (w/w) (more preferably at 6-8%) at 70° C. 0-10% (w/w) (more preferably 2-5%) Poly(L)glutamic acid (PLGA) (Sigma, St Louis, Mo.) and 1-Ethyl-3-(3-dimethylaminopropyl) carbodiimide (EDC) (Sigma) at 0, 2-15% (preferably 0.2-0.4%) were then added. The resultant hydrogel formed on stirring was left at room temperature for one hour. The hydrogel was allowed to swell in excess saline thr a fixed period of time (preferably 20 hr.) The hydrogel was then filtered by applying vacuum on a filter membrane (Millipore, Bedford, Mass.). The equilibrium swell was determined to be at least 1500% according to the method described in Example 10. The results are shown in Table 2.

TABLE 2

| Gelatin (mg) | PLGA (mg) | EDC | Swell (%) |
|---|---|---|---|
| 375 (6%) | 125 (2%) | 13.5 mg (.25%) | 1510 |
| 375 (6%) | 125 (2%) | 13.5 mg (.25%) | 1596 |
| 250 (4%) | 250 (4%) | 13.5 mg (.25%) | 2535 |
| 250 (4%) | 250 (4%) | 13.5 mg (.25%) | 2591 |
| 250 (4%) | 250 (4%) | 13.5 mg (.25%) | 2548 |
| 250 (4%) | 250 (4%) | 13.5 mg (.25%) | 2526 |
| 200 (3.2%) | 300 (4.8%) | 13.5 mg (.25%) | 2747 |
| 200 (3.2%) | 300 (4.8%) | 13.5 mg (.25%) | 2677 |
| 200 (3.2%) | 300 (4.8%) | 13.5 mg (.25%) | 2669 |
| 150 (2.4%) | 350 (5.6%) | 13.5 mg (.25%) | 3258 |
| 150 (2.4%) | 350 (5.6%) | 13.5 mg (.25%) | 3434 |
| 150 (2.4%) | 350 (5.6%) | 13.5 mg (.25%) | 3275 |
| 75 (5.5%) | 25 (1.9%) | 0.945 mg (0.35%) | 2437 |
| 50 (3.7%) | 50 (3.7%) | 0.945 mg (0.35%) | 2616 |
| 25 (1.9%) | 75 (5.5%) | 0.945 mg (0.35%) | 5383 |
| 75 (5.5%) | 25 (1.9%) | 9.45 mg (3.5%) | 1976 |
| 50 (3.7%) | 50 (3.7%) | 9.45 mg (3.5%) | 2925 |
| 25 (1.9%) | 75 (5.5%) | 9.45 mg (3.5%) | 4798 |

Example 14

Production of a Fragmented Polymeric Hydrogel

Bovine Corium (Spears Co. PA) was agitated in an aqueous sodium hydroxide (Spectrum Chemical Co., CA) solution (0.1 M to 1.5 M preferably 0.4 to 1.2M) for a period of one to 18 hours (preferably one to four hours) at a temperature of 2° C. to 30° C. (preferably 22° C. to 30° C.). The corium slurry was then neutralized using an inorganic acid such as hydrochloric acid, phosphoric acid or sulfuric acid (Spectrum Chemical Co., CA.) and the neutralized liquid phase was then separated from the insoluble corium by filtration through a sieve. The corium was then washed with non-pyrogenic water and an alcohol such as isopropyl alcohol (Spectrum Chemical Co., CA.). After three to twelve washes, the corium was suspended in non-pyrogenic water and the corium, water slurry may be then heated to 50° C. to 90° C. preferably 60° C. to 80° C. to thermally gelatinize the corium. During the gelatinization cycle, the pH of the corium, water slurry was adjusted and controlled from pH 3 to pH 11, preferably pH 7 to pH 9. Also, the insoluble corium in the slurry may be disrupted by agitation and/or homogenization. The disruption can occur before or after the thermal gelatinization cycle. Thermal gelatinization was conducted for one to six hours. After gelatinization, the slurry was clarified by filtration. The gelatin slurry was dewatered by drying in air at 15° C. to 40° C., preferably 20° C. to 35° C. The dry gelatin, where dry implies a moisture content less than 20% by weight, was then disrupted by grinding.

Dry gelatin was added to a cold (5° C. to 15° C.) aqueous solution of containing glutaraldehyde (Amresco Inc., OH.) at 0.0025% to 0.075% by weight and at a pH between 7 and 10. The concentration of gelatin in this solution was between 1% and 10% by weight. The glutaraldehyde cross-links the gelatin granules over a period of one to 18 hours after which the gelatin was separated from the aqueous phase by filtration or sedimentation. The gelatin particles were then added to an aqueous solution containing 0.00833% to 0.0667% by weight sodium borohydride (Spectrum. Chemical Co., CA.) with the gelatin concentration again being between % and 10% by weight and the pH being between 7 and 12, preferably 7 to 9. After one to six hours, the cross-linked gelatin was separated from the aqueous phase by filtration or sedimentation. The gelatin may then be resuspended in non-pyrogenic water with the gelatin concentration being between 1% and 10% by weight to remove residual cross-linking and reducing agents followed by separation from the aqueous phase by filtration or sedimentation. Final collection of the cross-linked gelatin was done on as filter mesh or sieve and the gelatin was given a final rinse with non-pyrogenic water. The wet. cross-linked gelatin was then placed in a drying chamber at 15° C. to 40° C. Dry, cross-linked gelatin (i.e. cross-linked gelatin with a moisture content below 20% by weight) was removed from the drying chamber and then ground using a mechanical, grinding, mill to produce a powder with a typical particle size distribution from 0.020 mm to 2.000 mm.

Dry, powdered, cross-linked gelatin was resuspended in a sodium phosphate, sodium chloride and sodium ascorbate buffer at pH 5 to 8 with the gelatin concentration being 10% to 20% by weight. The dry, powdered, cross-linked gelatin may be mixed with the buffer before dispensing the material into the applicator device (i.e. a syringe) or the powdered, cross-linked gelatin may be mixed with the buffer within the applicator device (i.e. a syringe). Additionally, a gas, such as air or nitrogen, may be dispersed with the gelatin and buffer to aid in mixing and dispensing of the material. The gas typically comprised less than 20% by volume of the final mixture.

Powdered, cross-linked gelatin, mixed with buffer and gas within an applicator device was then sealed in the kit to be supplied to the end user. The kits are sterilized by irradiation with gamma-rays or an electron beam.

Example 15

Preparation of Gelatin Powder

Strips of bovine corium were suspended in a sodium hydroxide solution of concentration 1 M to 2 M fir 1 hr at room temperature, neutralized with phosphoric acid and rinsed. The treated strips were then resuspended in deionized water, adjusted to pH 7-8, and heated to 70° C. A homogenizer was used to further reduce the size of the strips. After 1 hr at 70° C., the corium was largely solubilized to gelatin. The amount of corium was chosen so that the solids content of the resulting gelatin solution was approximately 3-10% (w/w), typically 7-10%. The solution was cast as thin layers onto Teflon® coated metal trays, dried, and ground to form gelatin powder.

Example 16

Preparation of "Modified Gelatin Powder"

Re-hydration aids (Table 1) were dissolved in 500 mL of 50° C. de-ionized water and then an amount of bovine derived gelatin powder, prepared as in Example 15, was added to the solution. The final concentration of gelatin in solution was chosen to be approximately 8% (w/w, bulk gelatin powder basis), and the total amount of re-hydration aids in the solution was chosen as in Examples 23-58 (Tables 3 and 4). After the gelatin had dissolved, the solution was poured into Teflon® coated metal trays and dried. The dried gelatin sheet is ground to form "modified gelatin powder".

Alternatively, strips of bovine corium were suspended in a sodium hydroxide solution of concentration 1 M to 2 M for 1 hr at room temperature, neutralized with phosphoric acid, and rinsed. The treated strips were then resuspended in deionized water, adjusted to pH 7-8, and heated to 70° C. A homogenizer was used to further reduce the size of the strips. After 1 hr at 70° C., the corium was largely solubilized to gelatin. The amount of corium was chosen so that the solids content of the resulting gelatin solution was approximately 3-10%

(w/w). typically 7-10%. Amounts of re-hydration aids were chosen as in Examples 23-58 (Tables 3 and 4) and were then added to the gelatin solution, either in solid form or dissolved in a small volume of water. The solution was cast into thin layers onto Teflon® coated metal trays, dried, and ground to form "modified gelatin powder". Examples of several formulations for modified gelatin are given in Tables 3 and 4.

Example 17

Preparation of Cross-Linked Gelatin Powder from "Modified Gelatin Powder"

600 mL of 0.2 M phosphate buffer (pH 9.2±0.2) was cooled to a temperature below 12° C. 0.32 mL of glutaraldehyde (25%) was added to the buffer solution and then 20 g of modified gelatin powder was added, resulting in a glutaraldehyde concentration of 4000 ppm (glutaraldehyde to modified gelatin, bulk weight basis). The gelatin was suspended in the glutaraldehyde solution with a stir bar. The pH of each suspensions was adjusted to a range of 9.2±0.2 and then maintained at a temperature of 9 to 12° C. and pH of 9.2±0.2 over 19 hours.

The suspension was filtered and the tiller cake was washed with de-ionized water three times by completely covering the filter cake with dc-ionized water and then allowing the vacuum to draw the rinse water through the cake. The filter cake was left in the funnel during each rinse.

0.2 g of NaBH4 was dissolved in 600 mL 25 mM phosphate buffer, pH 7.4 0.2, in a beaker. The above filter cake was suspended in the NaBH4 solution at room temperature (about 22° C.) for 3 hours, then filtered to remove the liquid.

The filler cake was next suspended in 600 mL of buffer solution at room temperature (about 22° C.) for 30 minutes and filtered again. The buffer was composed of sodium phosphate (dibasic anhydrous and monobasic monohydrate) and sodium ascorbate. The above procedure was repeated twice to ensure that the appropriate ratio of salts to gelatin. were present to form the desired buffer composition upon reconstitution. The filter cake was dried, then ground with a Waring Blender, resulting in "cross-linked gelatin powder". This method was also used to prepare cross-linked gelatin powder from unmodified gelatin powder; that is, gelatin to which no re-hydration aids were added during its preparation.

Example 18

Preparation of Irradiated Product from Cross-Linked Gelation Powder

About 800 mg (bulk weight) of the cross-linked gelatin powder, prepared as in Example 16, were put into each of several 5 cc syringes. The syringes containing powder were sterilized with gamma irradiation at ambient temperature.

Example 19

Use of Product as a Hemostatic Agent

A syringe of product containing approximately 0.8 g of irradiated cross-linked gelatin powder was prepared Limit modified gelatin powder. The modified gelatin powder was prepared as in Example 16. The modified gelatin was further cross-linked and irradiated as in Examples 17 and 18. The product was mixed with 4 mL of a saline solution containing about 1000 Units of bovine thrombin per milliliter. Mixing was achieved by passage back and forth between two syringes connected with a female-female straight-through Liter connector. The powder in the syringe was hydrated as it mixed with the thrombin solution, forming granules of hydrogel.

A square lesion, approximately 1 cm×1 cm×0.2 cm deep, was created on the liver of a farm-grade pig. The pig had been anticoagulated with heparin so that its activated clotting time (ACT) was three to five times its baseline value, and the lesion bled freely prior to treatment. After about 30 seconds from the start of mixing, approximately 2 mL of the hydrated powder was extruded from the syringe onto the lesion and held in place with compression for two minutes. After compression was removed, the treated lesion was observed for bleeding at 3 min, 10 min, and 50 min after application. No bleeding was seen from the treated lesion at the 3 min and 10 min observation. After the 10 min observation, the treated lesion was irrigated with saline solution. While excess material was removed, no re-bleeding was observed. At 50 min after application, the lesion was observed again and no bleeding was seen.

Example 20

Determination of Re-Hydration Rate of a Powder

The "re-hydration rate" of a powder was measured as follows. The powder, packed in a 5 cc syringe, was mixed with a syringe containing a volume of aqueous solution by passage between the two syringes connected with a Luer fitting for 30 seconds. The volume of aqueous solution was chosen to be in excess of what could be expected to be absorbed in 30 seconds. Typically, 0.8 g (bulk weight) of powder was mixed with 3 mL of 0.9% sodium chloride solution. The resulting mixture was then immediately filtered to remove any unabsorbed liquid. The wet filtered material was weighed, then dried in a 120° C. oven for two hours and re-weighed. This measurement gave the total amount of water removed from the wet material and the weight of the dry powder. The amount of water that had been absorbed by the powder was then calculated after a small correction is made for the residual moisture that had been present in the powder originally. The "re-hydration rate" was given as the mass of saline solution absorbed per gram dry weight of powder in that 30 second interval.

In the calculation below, the fraction solids of the bulk powder ("S") was measured independently by drying the bulk powder at 120° C. for 2 hr and weighing the powder before and after drying. The value of S is given by the following:

$$S = \frac{\text{weight after drying at } 120° \text{ C., 2 hr}}{\text{weight before drying}}$$

Re-hydration rate calculation:
A: initial weight of the pan and filter paper
B: weight of the pan, filter paper and hydrated powder
C: weight of the pan, filter paper and sample after drying, in oven
S: fraction solids of the bulk powder originally in syringe
M: grams of saline absorbed per gram of powder (dry weight) during mixing ("absorption rate")

$$M = \frac{(B-A) - (C-A)/S}{(C-A)}$$

Example 21

Re-Hydration Rate and Physical Property Determination for Several Batches of Powder Product Tables 3 and 4 depict the results of re-hydration rate measurements performed on one to for several batches of powder product (Examples 23-37). These were made using methods as per Examples 15, 16, 17, and 18. Except for Examples 23 and 31, these were prepared from modified gelatins that were made with various proportions of gelatin and the following re-hydration aids: polyethylene glycol (PEG), average molecular weight 1000; polyvinylpyrrolidone (PVP), "k-30" designation, corresponding to an average molecular weight of about 50,000; and dextran, average molecular weight 40,000. It is seen that use of several different combinations of gelatin and re-hydration aids can result in a powder product that absorbs more aqueous saline solution in 30 seconds per gram of powder than powder product made from gelatin to which no re-hydration aids have been added. It is also seen that the combination of gelatin, PEG. PVP and dextran at a bulk weight ratio of 80:10:5:5 in the modified gelatin (Example 24) produces a powder product that absorbs about 33% more saline solution per gram in 30 seconds than powder product made from unmodified gelatin.

Table 3 also gives values for other physical properties determined for the powder product lots. "Percent solids" was determined by weighing the powder before and after drying at 120° C. for two hours to drive off residual moisture. "DSC peak temperature" refers to the temperature at which a peak is exhibited in a thermogram of a differential scanning calorimetry measurement conducted from 1° C. to 70° C., "Equilibrium swell" was determined by suspending the powder in an excess of saline solution for at least 18 hr at room temperature. The hydrated powder was weighed to determine its "equilibrium wet weight" and dried at 120° C. for two hours and re-weighed to determine its "dry weight". Equilibrium swell is given as $$\text{Equilibrium swell } (\%) = 100\% \times \frac{\text{equilibrium wet weight} - \text{dry weight}}{\text{dry weight}}$$

Values for "mean particle size" were measured by light scattering in a Coulter LS particle size analyzer.

From the data presented in Table 3, it appears that the appropriate use of re-hydration aids can change the re-hydration rate of the powder product without significantly changing other physical properties.

Example 22

Measurement of Polyethylene Glycol, Polyvinylpyrrolidone, and Dextran Levels in Modified Gelatin Powder and in Cross-Linked Powder Approximately 50 mg modified gelatin or 250 mg cross-linked irradiated powder product were suspended in 10 mL of deionized, water and heated for 3 hr at 65*C. The samples were then centrifuged at 15 minutes at 2000 rpm. The resulting supernatant was filtered through a 0.45 μm Gelman Acrodisc filter, the first mL being discarded. The resulting sample was then assayed by three different high performance liquid chromatography (HPLC) methods to quantitate the polyethylene glycol (PEG), polyvinylpyrrolidone (PVP), and dextran in the sample. For PEG, 100 μL of the sample was injected onto a Waters Ultrahydrogel 120 column, 7.8×300 mm, with guard column and prefilter, using deionized water as the mobile phase. A refractive index detector was used to monitor the effluent. For PVP, 100 μL of the sample was injected onto a Phenomenex Kingsorb C18 5 μm column, 4.6×150 mm, with guard column and prefilter, using a gradient of methanol and aqueous sodium phosphate as the mobile phase. An ultra-violet absorbance detector was used to monitor the effluent. For dextran, 100 μL, of the sample was injected onto a Waters Uhrahydrogel Linear column, 78×300 mm, with guard column and prefilter, using 0.1 M sodium phosphate, pH 7 and acetonitrile at a 90:10 ratio as the mobile phase. A refractive index detector was used to monitor the effluent. All columns were heated to 40° C. for the analyses. The limit of quantitation was about 0.1% (w/w sample) fir PEG and PVP, 0.2% (w/w sample) for dextran.

Modified gelatin was prepared as per Example 16. The modified gelatin was analyzed for PEG, PVP and dextran in the manner described above. Results indicated that PEG. PVP, and dextran were present at 16%, 8%, and 3% (w/w bulk; respectively. The modified gelatin was subsequently subjected to cross-linking, sodium borohydride treatment, and rinsing as per Example 17 to form cross-linked modified gelatin powder. When this powder was analyzed for PEG, PVP, and dextran by HPLC in the manner described above, the content of each of the three re-hydration aids was found to be below the limit of quantitation.

Example 23

Powder Product Made without Re-Hydration Aids

Unmodified gelatin—that is, gelatin to which processing aids were not added—was prepared from bovine corium strips as in Example 15 and cross-linked as in Example 17. The cross-linked unmodified gelatin was then packed into syringes and gamma irradiated as in Example 18. Physical properties of the resulting product were measured as in Examples 20 and 21 and are given in Table 3.

Examples 24-37

Powder Product Made with Re-Hydration Aids

Batches of modified gelatin were prepared as in Example 16 from gelatin powder or corium strips and from one, two, or three re-hydration aids. Table 3 gives the proportions of bulk gelatin and re-hydration aids used. The modified gelatin was then cross-linked as in Example 17. Except for Example 31, the re-hydration aids used were from the following list: polyethylene glycol (PEG) of an average molecular weight of about 1000; polyvinylpyrrolidone (PVP), "k-30" designation, of an average molecular weight of about 50,000; and dextran, of an average molecular weight of about 40,000. In Example 31, PEG of an average molecular weight of about 400 was used. The cross-linked modified gelatin was then packed into syringes and gamma irradiated as in Example 18. Physical properties of the resulting powder product from each of these preparations were measured as in Examples 20 and 21 and are given in Table 3. Data given with the formulation for Example 24 is the average and standard deviation of nine batches prepared according to that formulation.

Examples 38-58

Powder Product Made with Various Re-Hydration Aids

Batches of modified gelatin were prepared as in Example 16 from gelatin powder or corium strips and from one of several re-hydration aids. Table 4 gives the identity and concentration of re-hydration aid used in each batch as a ratio of bulk gelatin weight to re-hydration aid and as a percentage of total hulk solute used to prepare the modified gelatin. The modified gelatin was then cross-linked as in Example 17. The cross-linked modified gelatin was then packed into syringes and gamma irradiated as in Example 18. Physical properties of the resulting powder product from each of these preparations were measured as in Examples 20 and 21 and are given in Table 4. Data for the Example 23 formulation is provided in Table 4 for comparison.

TABLE 3

| | Lot | Target bulk weight percent in modified gelatin | | | | Properties of powder product after cross-linking and gamma irradiation (re-hydration aids largely removed) | | | | |
|---|---|---|---|---|---|---|---|---|---|---|
| | | Gelatin (bulk weight) | PEG MW = 1000 D | PVP MW ~50000 D | Dextran MW = 40000 D | % solids | DSC peak temp (° C.) | Equilibrium swell (%) | Mean particle size (μm) | Re-hydration* |
| No re-hydration aids added | | | | | | | | | | |
| Example 23 Preferred composition (four-way mixture) | 208-32 | 100 | 0 | 0 | 0 | 88.6 | 41.3 | 551 | 440 | 2.85 |
| Example 24 | avg of 9 lots | 80 | 10 | 5 | 5 | 87.6 | 42.1 | 595 | 423 | 3.79 |
| | std. deviation of 9 lots | | | | | 1.0 | 1.4 | 43 | 65 | 0.15 |
| Three-way mixtures | | | | | | | | | | |
| Example 25 | 228-69-1 | 80 | 10 | 10 | 0 | 88.1 | 40.8 | 667 | 387 | 3.51 |
| Example 26 | 228-69-2 | 80 | 10 | 0 | 10 | 88.4 | 40.6 | 670 | 367 | 3.14 |
| Example 27 | 228-78 | 80 | 0 | 10 | 10 | 86.7 | 41.1 | 632 | 414 | 3.20 |
| Gelatin-PEG mixtures | | | | | | | | | | |
| Example 28 | 212-39-2 | 94 | 6 | 0 | 0 | 86.2 | 44.4 | 502 | 372 | 2.68 |
| Example 29 | 228-42-3 | 89 | 11 | 0 | 0 | 88.6 | 42.8 | 594 | 428 | 3.16 |
| Example 30 | 228-42-1 | 80 | 20 | 0 | 0 | 88.9 | 42.4 | 575 | 312 | 3.47 |
| Example 31 | 214-62-1 | 89 | 11** | 0 | 0 | 87.1 | 40.7 | 599 | 406 | 3.11 |
| Gelatin-PVP mixtures | | | | | | | | | | |
| Example 32 | 228-38-3 | 94 | 0 | 6 | 0 | 88.2 | 42.2 | 567 | 399 | 3.26 |
| Example 33 | 228-38-2 | 89 | 0 | 11 | 0 | 88.3 | 41.0 | 605 | 422 | 3.44 |
| Example 34 | 228-38-1 | 80 | 0 | 20 | 0 | 88.6 | 42.4 | 596 | 401 | 3.52 |
| Gelatin-dextran mixtures | | | | | | | | | | |
| Example 35 | 228-35-3 | 94 | 0 | 0 | 6 | 88.1 | 40.5 | 631 | 395 | 3.18 |
| Example 36 | 228-35-2 | 89 | 0 | 0 | 11 | 88.3 | 41.4 | 598 | 345 | 3.03 |
| Example 37 | 228-35-1 | 80 | 0 | 0 | 20 | 88.5 | 41.9 | 624 | 392 | 3.01 |

*Re-hydration rate defined as grams saline absorbed per gram power product (dry wt) in 30 sec
**PEG (MW = 400) used instead of MW = 1000

TABLE 4

| | | | Re-hydration aid | | | | | | |
|---|---|---|---|---|---|---|---|---|---|
| | | | | | Conc'n of processing aid in modified gelatin (bulk wt %) | Physical properties | | | |
| | Lot | type | MW or other designation | bulk gelatin wt: aid | | % solids | DSC peak temp (° C.) | Equilibrium swell (%) | Mean particle size (μm) | Re-hydration rate* |
| Example 23 | 208-32 | no re-hydration aids | | | | 88.6 | 41.3 | 551 | 440 | 2.85 |
| Example 38 | 214-11-1 | glycerol | n/a | 4 | 20% | 85.5 | 43.4 | 483 | 653 | 2.19 |
| Example 39 | 214-11-2 | glycerol | n/a | 8 | 11% | 86.4 | 43.4 | 529 | 421 | 2.62 |
| Example 40 | 214-11-3 | glycerol | n/a | 16 | 6% | 86.5 | 43.0 | 543 | 398 | 2.35 |
| Example 41 | 214-44-1 | dextran | 148000 D | 4 | 20% | 85.5 | nr | 634 | 433 | 2.62 |
| Example 42 | 214-44-2 | dextran | 148000 D | 8 | 11% | 85.4 | nr | 607 | 453 | 2.57 |
| Example 43 | 214-44-3 | dextran | 148000 D | 16 | 6% | 85.5 | nr | 603 | 527 | 2.33 |
| Example 44 | 214-44-4 | dextran | 148000 D | 32 | 3% | 85.7 | nr | 531 | 491 | 2.37 |
| Example 45 | 228-35-4 | dextran | 40000 D | 32 | 3% | 84.5 | 41.4 | 633 | 380 | 2.59 |
| Example 46 | 214-50-1 | PVP | k-90 | 4 | 20% | 85.3 | 44.0 | 612 | 664 | 2.41 |
| Example 47 | 214-50-2 | PVP | k-90 | 8 | 11% | 85.6 | 44.3 | 538 | 581 | 2.71 |
| Example 48 | 214-50-3 | PVP | k-90 | 16 | 6% | 85.6 | 44.1 | 527 | 593 | 2.78 |

TABLE 4-continued

|  | Lot | Re-hydration aid | | | Conc'n of processing aid in modified gelatin (bulk wt %) | Physical properties | | | | |
|---|---|---|---|---|---|---|---|---|---|---|
|  |  | type | MW or other designation | bulk gelatin wt: aid |  | % solids | DSC peak temp (° C.) | Equilibrium swell (%) | Mean particle size (μm) | Re-hydration rate* |
| Example 49 | 214-50-4 | PVP | k-90 | 32 | 3% | 86.1 | 43.0 | 597 | 538 | 2.76 |
| Example 50 | 214-53-4 | PVP | k-30 | 32 | 3% | 87.3 | 41.1 | 580 | 447 | 2.72 |
| Example 51 | 214-59-1 | PEG | 400 | 4 | 20% | 86.7 | 42.0 | 595 | 407 | 2.18 |
| Example 52 | 214-66-1 | PEG | 400 | 6 | 14% | 86.5 | 40.8 | 603 | 501 | 2.63 |
| Example 53 | 212-39-1 | PEG | 400 | 16 | 6% | 86.2 | 43.8 | 513 | 403 | 2.11 |
| Example 54 | 212-39-2 | PEG | 1000 | 16 | 6% | 86.2 | 44.4 | 502 | 372 | 2.68 |
| Example 55 | 214-59-3 | PEG | 8000 | 4 | 20% | 87.4 | 41.5 | 548 | 429 | 2.87 |
| Example 56 | 214-66-3 | PEG | 8000 | 6 | 14% | 86.9 | 41.4 | 581 | 426 | 3.80 |
| Example 57 | 214-62-3 | PEG | 8000 | 8 | 11% | 86.8 | 42.0 | 631 | 511 | 2.78 |
| Example 58 | 212-39-3 | PEG | 8000 | 16 | 6% | 86.4 | 44.6 | 546 | 518 | 2.72 | nr = not reported
*Re-hydration rate defined as grams saline absorbed per gram powder product (dry wt) in 30 sec Although the foregoing invention has been described in some detail by way of illustration and example, for purposes of clarity of understanding, it will be obvious that certain changes and modifications may be practiced within the scope of the appended claims.

What is claimed is:

1. A method of treating a patient with a hemostatic composition, the method comprising:
   delivering the hemostatic composition to a treatment site of the patient,
   wherein the hemostatic composition comprises a mixture containing an amount of thrombin and an amount of resorbable fragmented cross-linked gelatin gel having an equilibrium swell value within a range from 400% to 1300%.

2. The method according to claim 1, wherein the treatment site is a bleeding site or bleeding tissue surface of a patient, or an abraded or damaged tissue surface of a patient.

3. The method according to claim 1, wherein the delivery step includes extruding the mixture from a syringe to the treatment site.

4. The method according to claim 2, wherein the tissue surface comprises an organ surface selected from the group consisting of a liver surface, a spleen surface, a heart surface, a kidney surface, an intestine surface, a blood vessel surface, and a vascular organ surface.

5. The method according to claim 2, comprising delivering the hemostatic composition to the bleeding site or bleeding tissue surface of the patient.

6. The method according to claim 2, comprising delivering the hemostatic component to the abraded or damaged tissue surface.

7. A method of treating a patient with a hemostatic composition, the method comprising:
   delivering the hemostatic composition from a syringe to a treatment site of the patient,
   wherein the hemostatic composition comprises a mixture containing an amount of aqueous buffer and an amount of resorbable fragmented cross-linked gelatin gel having an equilibrium swell value within a range from 400% to 1300%.

8. The method according to claim 7, wherein the aqueous buffer comprises sodium phosphate.

9. The method according to claim 7, wherein the aqueous buffer comprises sodium chloride.

10. A method of treating a patient with a hemostatic composition, the method comprising:
    delivering the hemostatic composition from a syringe to a treatment site of the patient,
    wherein the hemostatic composition comprises a mixture containing an amount of sterile saline for injection and an amount of resorbable fragmented cross-linked gelatin gel having an equilibrium swell value within a range from 400% to 1300%.

11. A method of treating a patient with a hemostatic composition, the method comprising:
    delivering the hemostatic composition from a syringe to a target site of the patient,
    wherein the hemostatic composition comprises a mixture containing an amount of sterile water and an amount of resorbable fragmented cross-linked gelatin gel having an equilibrium swell value within a range from 400% to 1300%.

12. The method according to claim 11, wherein the gelatin gel is at least partially hydrated.

13. A method of treating a patient with a hemostatic composition, the method comprising:
    delivering the hemostatic composition from a syringe to a treatment site of the patient,
    wherein the hemostatic composition comprises a mixture containing an amount of aqueous medium and an amount of resorbable fragmented cross-linked gelatin gel having an equilibrium swell value within a range from 400% to 1300%.

14. The method according to claim 1, wherein the hemostatic composition consists essentially of the mixture containing the amount of thrombin and the amount of resorbable fragmented cross-linked gelatin gel.

15. The method according to claim 7, wherein the hemostatic composition consists essentially of the mixture containing the amount of aqueous buffer and the amount of resorbable fragmented cross-linked gelatin gel.

16. The method according to claim 10, wherein the hemostatic composition consists essentially of the mixture containing the amount of sterile saline for injection and the amount of resorbable fragmented cross-linked gelatin gel.

17. The method according to claim 11, wherein the hemostatic composition consists essentially of the mixture containing the amount of sterile water and the amount of resorbable fragmented cross-linked gelatin gel.

18. The method according to claim 13, wherein the hemostatic composition consists essentially of the mixture containing the amount of aqueous medium and the amount of resorbable fragmented cross-linked gelatin gel.

* * * * *

UNITED STATES PATENT AND TRADEMARK OFFICE
CERTIFICATE OF CORRECTION

| | | |
|---|---|---|
| PATENT NO. | : 8,512,729 B2 | Page 1 of 1 |
| APPLICATION NO. | : 13/665475 | |
| DATED | : August 20, 2013 | |
| INVENTOR(S) | : Donald G. Wallace et al. | |

It is certified that error appears in the above-identified patent and that said Letters Patent is hereby corrected as shown below:

1) On the Title Page, item (63), Line 5 of that paragraph, please delete "-in-part".

Signed and Sealed this
Twenty-second Day of October, 2013

Teresa Stanek Rea
*Deputy Director of the United States Patent and Trademark Office*